US011147855B2

(12) United States Patent
Schiffman et al.

(10) Patent No.: US 11,147,855 B2
(45) Date of Patent: Oct. 19, 2021

(54) METHODS FOR TREATING GLAUCOMA OR OCULAR HYPERTENSION COMPRISING DELIVERY OF PROSTAGLANDINS TO THE VITREOUS HUMOUR

(71) Applicant: Cella Therapeutics, LLC, Miami, FL (US)

(72) Inventors: Rhett M. Schiffman, Laguna Beach, CA (US); Lukas Scheibler, Laguna Beach, CA (US)

(73) Assignee: Cella Therapeutics, LLC, Miami, FL (US)

( * ) Notice: Subject to any disclaimer, the term of this patent is extended or adjusted under 35 U.S.C. 154(b) by 101 days.

(21) Appl. No.: 16/719,703

(22) Filed: Dec. 18, 2019

(65) Prior Publication Data
US 2020/0108117 A1    Apr. 9, 2020

Related U.S. Application Data

(63) Continuation-in-part of application No. PCT/US2019/037774, filed on Jun. 18, 2019.

(60) Provisional application No. 62/687,172, filed on Jun. 19, 2018, provisional application No. 62/726,029, filed on Aug. 31, 2018, provisional application No. 62/747,060, filed on Oct. 17, 2018.

(51) Int. Cl.
| | | |
|---|---|---|
| A61K 38/08 | (2019.01) | |
| A61K 31/557 | (2006.01) | |
| A61P 27/06 | (2006.01) | |
| A61K 31/192 | (2006.01) | |
| A61K 38/07 | (2006.01) | |
| A61K 47/64 | (2017.01) | |
| A61K 47/55 | (2017.01) | |
| A61K 31/165 | (2006.01) | |
| A61K 38/17 | (2006.01) | |
| A61K 38/22 | (2006.01) | |
| A61K 45/06 | (2006.01) | |

(52) U.S. Cl.
CPC .......... *A61K 38/08* (2013.01); *A61K 31/165* (2013.01); *A61K 31/192* (2013.01); *A61K 31/557* (2013.01); *A61K 38/07* (2013.01); *A61K 38/1796* (2013.01); *A61K 38/22* (2013.01); *A61K 45/06* (2013.01); *A61K 47/55* (2017.08); *A61K 47/64* (2017.08); *A61K 47/6425* (2017.08); *A61P 27/06* (2018.01)

(58) Field of Classification Search
None
See application file for complete search history.

(56) References Cited

U.S. PATENT DOCUMENTS

| | | | | |
|---|---|---|---|---|
| 2007/0224247 A1* | 9/2007 | Chudzik | ............... | A61L 27/20 424/427 |
| 2008/0089923 A1* | 4/2008 | Burkstrand | ........... | A61F 9/0017 424/428 |
| 2010/0278931 A1* | 11/2010 | Ashton | ................ | A61K 9/0097 424/501 |
| 2014/0186420 A1* | 7/2014 | Utkhede | ................ | A61P 43/00 424/427 |
| 2016/0106667 A1* | 4/2016 | Kopczynski | ......... | A61K 9/0051 424/427 |
| 2016/0151386 A1* | 6/2016 | Wong | ................... | A61K 9/0048 514/530 |
| 2016/0302965 A1* | 10/2016 | Erickson | ............ | A61K 31/5575 |
| 2018/0280194 A1* | 10/2018 | Heitzmann | .......... | A61K 9/0051 |

OTHER PUBLICATIONS

Tham et al., "Global Prevalence of Glausoma and Projects of Glaucoma Burden through 2040, A Systematic Review and Meta-Analysis", American Academy of Ophthalmology, vol. 121, No. 11, 2081-2090, bearing an alleged date of Nov. 2014.
Flaxman et al., "Global causes of blindness and distance vision impairment 1990-2020: a systematic review and meta-analysis", The Lancet Global Health, vol. 5, e1221-34, bearing an alleged date of Dec. 2017.
Reardon et al., "Patient Persistency With Topical Ocular Hypotensive Therapy in a Managed Care Population", American Journal of Ophthalmology, vol. 137, No. 1, S3-S12, bearing an alleged date of Jan. 2004.
Hale, "Alcon pulls eye micro-stent from market after new 5-year safety data", https://www.fiercebiotech.com/medtech/alcon-pulls-eye-micro-stent-from-market-after-new-5-year-safety-data, MedTech, bearing an alleged date of Aug. 30, 2018.
Durysta™, "Highlights of Prescribing Information", Allergan USA, Inc., Reference ID: 4570587, NDA 211911, 4-13, bearing an alleged date of Mar. 2020.
Lumigan®, "Highlights of Prescribing Information", Allergan USA, Inc., Reference ID: 3101703, NDA 21-275/S-023, 3-10, bearing an alleged date of Mar. 2012.
Vyzulta, "Highlights of Prescribing Information", Bausch + Lomb, a division of Valeant Pharmaceuticals North America LLC, Reference ID: 4175996, NDA 21-275/S-023, 1-8, bearing an alleged date of Nov. 2017.

(Continued)

*Primary Examiner* — Kevin S Orwig
(74) *Attorney, Agent, or Firm* — Maschoff Brennan; Brent A. Johnson; David Old

(57) ABSTRACT

This disclosure relates to a drug delivery system comprising an intraocular pressure lowering agent, a neurotrophic agent, such as a CNTF compound, a C-type Natriuretic Peptide (CNP) compound, a Tie-2 agonist, a Natriuretic Peptide Receptor-B (NPR-B) compound, or an apoptosis signaling fragment inhibitor (FAS) or FAS-ligand (FASL) inhibitor, including any combination of these compounds and a sustained delivery component. Methods of treating a glaucoma or related conditions, medicaments, kits, uses and methods of manufacturing are also described.

19 Claims, 5 Drawing Sheets

Specification includes a Sequence Listing.

(56) References Cited

OTHER PUBLICATIONS

Sharif et al., "Agonist Activity of Bimatoprost, Travoprost, Latanoprost, Unoprostone Isopropyl Ester and Other Prostaglandin Analogs at the Cloned Human Ciliary Body FP Prostaglandin Receptor", Journal of Ocular Pharmacology and Therapeutics, vol. 18, No. 4, 313-324, bearing an alleged date of 2002.

* cited by examiner

SEQUENCE LISTING

```
<160> NUMBER OF SEQ ID NOS: 20

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Gly Asp Gly Gly Leu Phe Glu Lys Lys Leu
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Gly Gly Leu Gly
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His His Ile Tyr Leu Gly Ala Val Asn Tyr Ile Tyr
1               5                   10

<210> SEQ ID NO 4
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 4

His His Ile Tyr Leu Gly Ala Thr Asn Tyr Ile Tyr
1               5                   10

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Leu Gly Ala
1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Tyr Leu Gly Ala
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Leu Gly Ala Val
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Ile Tyr Leu Gly Ala
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Tyr Leu Gly Ala Val
1               5
```

```
<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Ile Tyr Leu Gly Ala Val
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Tyr Leu Gly Ala Val Asn
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His His Ile Tyr Leu Gly Ala
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Leu Gly Ala Val Asn Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His His Ile Tyr Leu Gly Ala Val
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 15

Tyr Leu Gly Ala Val Asn Tyr Ile
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Leu Gly Ala Val Asn
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His Ile Tyr Leu Gly Ala Val Asn
1               5

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term resin
<220> FEATURE:
<221> NAME/KEY: MOD_RES
<222> LOCATION: (2)..(3)
<223> OTHER INFORMATION: Lys(Boc)
<220> FEATURE:
<221> NAME/KEY: MOD_RES
<222> LOCATION: (4)..(4)
<223> OTHER INFORMATION: Glu(tBu)
<220> FEATURE:
<221> NAME/KEY: MOD_RES
<222> LOCATION: (9)..(9)
<223> OTHER INFORMATION: Asp(tBu)
<220> FEATURE:
<223> OTHER INFORMATION: C-term CO2(CH2-CH2-O)n-CH2-CH2-NH2

<400> SEQUENCE: 18

Leu Lys Lys Glu Phe Leu Gly Gly Asp Gly Val
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term resin
<220> FEATURE:
<221> NAME/KEY: MOD_RES
<222> LOCATION: (2)..(3)
<223> OTHER INFORMATION: Lys(Cbz)
<220> FEATURE:
```

```
-continued

<221> NAME/KEY: MOD_RES
<222> LOCATION: (4)..(4)
<223> OTHER INFORMATION: Glu(Bn)
<220> FEATURE:
<221> NAME/KEY: MOD_RES
<222> LOCATION: (9)..(9)
<223> OTHER INFORMATION: Asp(Bn)
<220> FEATURE:
<223> OTHER INFORMATION: C-term CO2(CH2-CH2-O)n-CH2-CH2-OH

<400> SEQUENCE: 19

Leu Lys Lys Glu Phe Leu Gly Gly Asp Gly Val
1               5                   10

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Gly Gly Leu
1
```

METHODS FOR TREATING GLAUCOMA OR OCULAR HYPERTENSION COMPRISING DELIVERY OF PROSTAGLANDINS TO THE VITREOUS HUMOUR

CROSS-REFERENCE TO RELATED APPLICATIONS

This application is a continuation-in-part of PCT/US2019/037774, filed Jun. 18, 2019, which claims the benefit of U.S. Provisional Application Nos. 62/687,172, filed Jun. 19, 2018, 62/726,029, filed Aug. 31, 2018, and 62/747,060, filed Oct. 17, 2018, all of which are incorporated by reference herein in their entirety. PCT/US2019/037791, filed Jun. 18, 2019, is also incorporated by reference herein in its entirety.

SEQUENCE LISTING

The instant application contains a Sequence Listing which has been submitted electronically in ASCII format and is hereby incorporated by reference in its entirety. Said ASCII copy, created on Dec. 17, 2019, is named C4019_10001US04_SL.txt and is 5,399 bytes in size.

SUMMARY

This disclosure relates to a drug delivery system comprising an intraocular pressure lowering agent, a neurotrophic agent, such as a CNTF compound, a C-type Natriuretic Peptide (CNP) compound, a Tie-2 agonist, a Natriuretic Peptide Receptor-B (NPR-B) compound, or an apoptosis signaling fragment inhibitor (FAS) or FAS-ligand (FASL) inhibitor, including any combination of these compounds and a sustained delivery component. This type of drug delivery system can be used to treat a glaucoma or ocular hypertension.

Some embodiments include a drug delivery system comprising: a first active pharmaceutical ingredient (API) and a sustained delivery component, wherein the first API is an intraocular pressure lowering agent, a neurotrophic agent, a C-type Natriuretic Peptide (CNP), a Natriuretic Peptide Receptor-B (NPR-B), an apoptosis signaling fragment (FAS) inhibitor or a FAS-ligand (FASL) inhibitor, or a combination thereof.

Some embodiments include a method of treating a glaucoma comprising administering a drug delivery system of described herein to a mammal in suffering from glaucoma or ocular hypertension.

Some embodiments include use of an intraocular pressure lowering agent, a neurotrophic agent, a CNP, an NPR-B, a FAS inhibitor or a FASL inhibitor, or a combination thereof, in the manufacture of a drug delivery system described herein for the treatment of glaucoma or ocular hypertension.

Some embodiments include a kit comprising a drug delivery system described herein and a label with instructions for use of the drug delivery system for the treatment of a glaucoma.

DETAILED DESCRIPTION

Figure 1A:
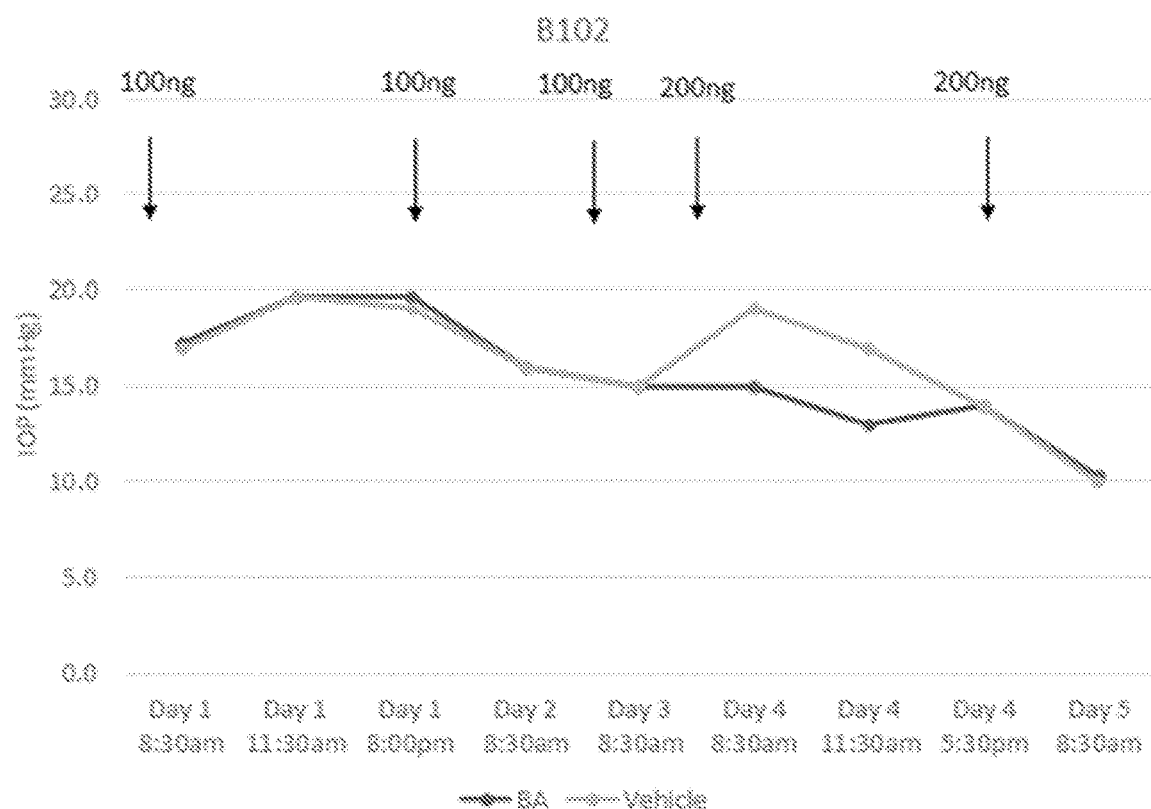
FIG. 1A is the intraocular pressure of the IOP for African Green Monkey B102 following administration of 100 ng and 200 ng bimatoprost acid by intravitreal injection compared with PBS in the fellow eye as related to some embodiments described herein.
Figure 1B:
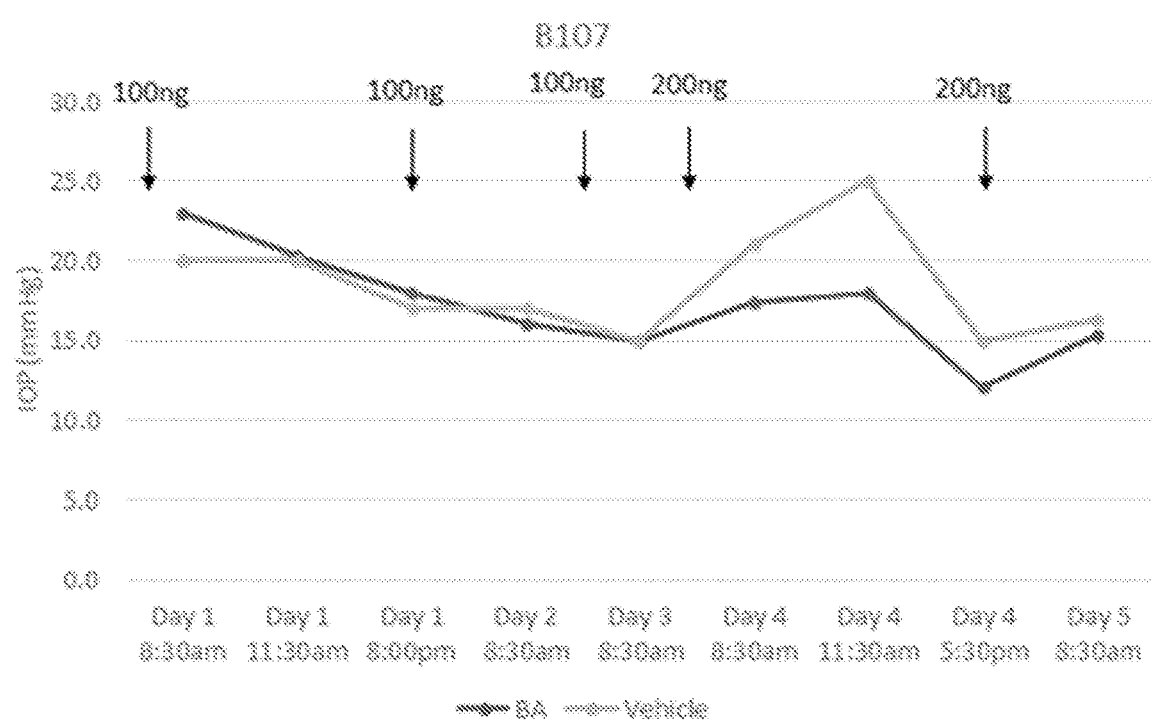
FIG. 1B is the intraocular pressure of the IOP for African Green Monkey B107 following administration of 100 ng and 200 ng bimatoprost acid by intravitreal injection compared with PBS in the fellow eye as related to some embodiments described herein.
Figure 1C:
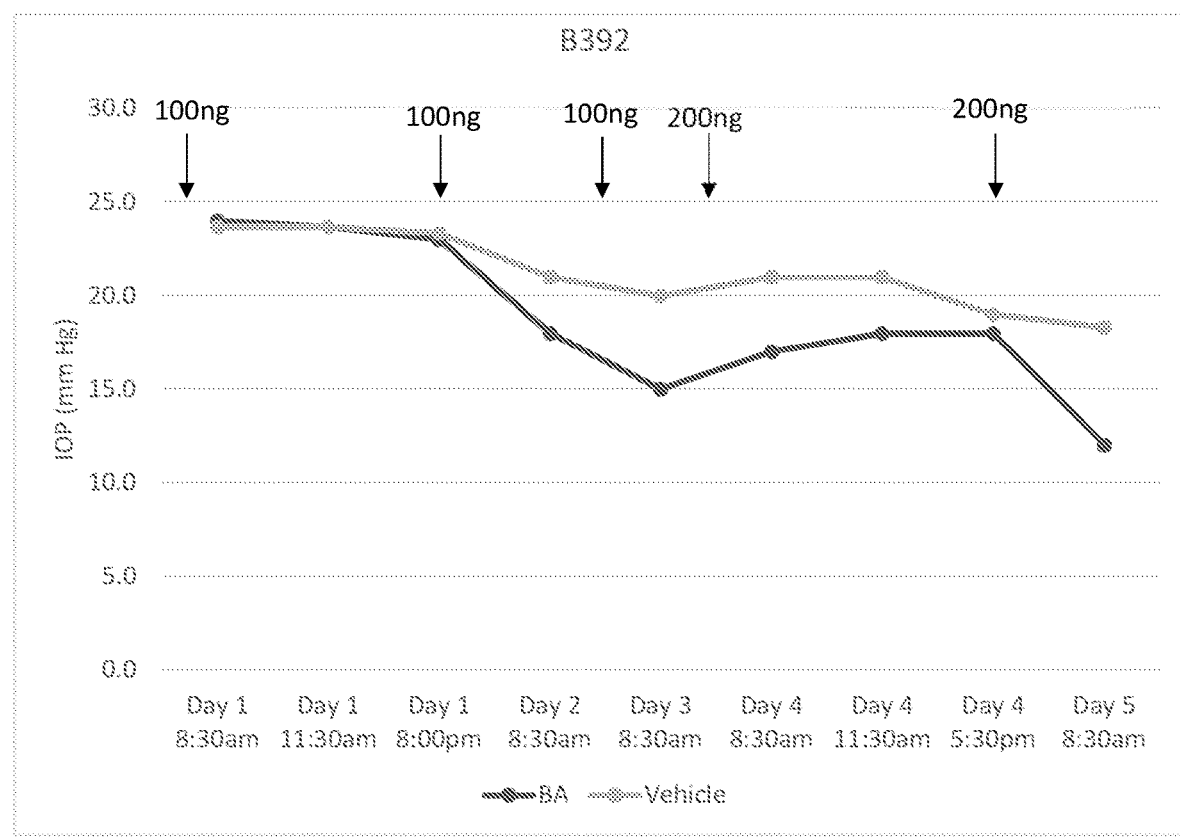
FIG. 1C is the intraocular pressure of the IOP for African Green Monkey B392 following administration of 100 ng and 200 ng bimatoprost acid by intravitreal injection compared with PBS in the fellow eye as related to some embodiments described herein.
Figure 1D:
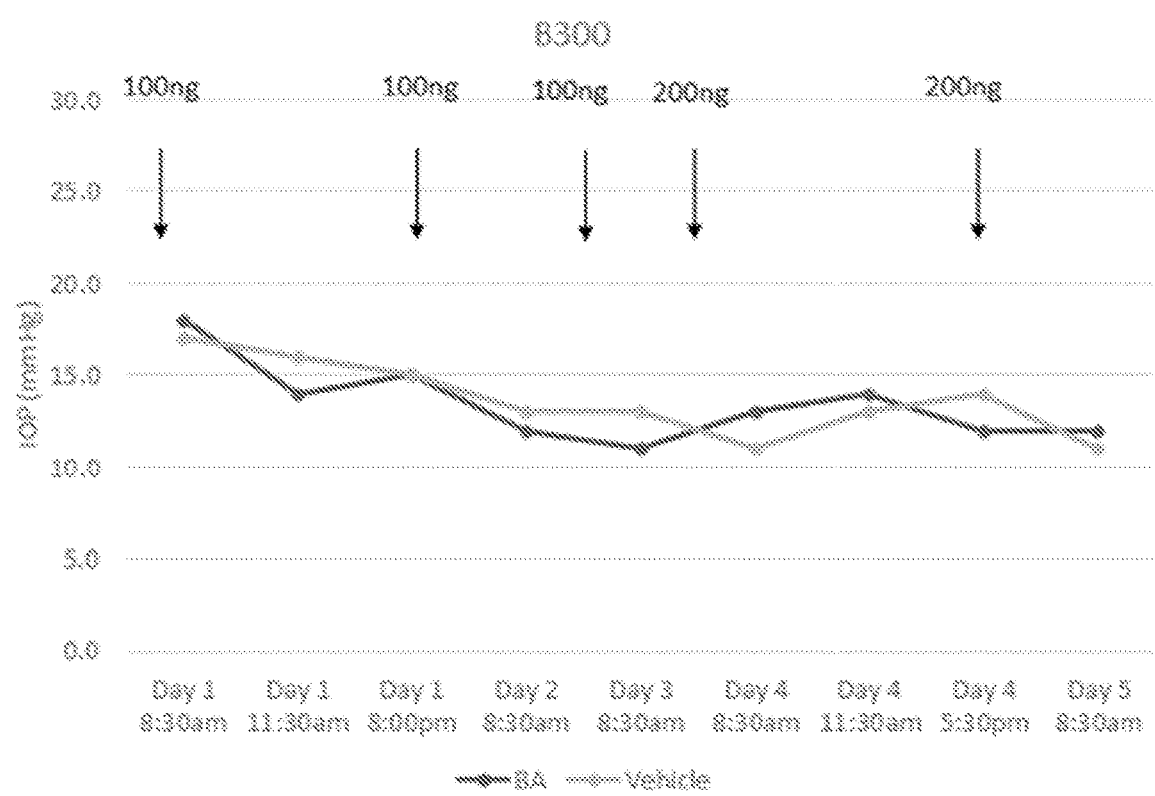
FIG. 1D is the intraocular pressure of the IOP for African Green Monkey B300 following administration of 100 ng and 200 ng bimatoprost acid by intravitreal injection compared with PBS in the fellow eye as related to some embodiments described herein.

With respect to a drug delivery system comprising an intraocular pressure lowering agent, a neurotrophic agent, such as a CNTF compound, a CNP compound, a NPR-B compound, or a FAS or FASL inhibitor (referred to herein as "subject drug delivery system"), and a sustained delivery component, any suitable prostaglandin receptor agonist, prostanoid receptor agonist, or any suitable prostaglandin compound, including any prostaglandin acid form (e.g. the acid obtained by hydrolyzing prostaglandin esters), any prostaglandin salt form, or any prostaglandin ester prodrug, may be used. Examples include bimatoprost (amide) or the bimatoprost acid, i.e. the carboxylic acid obtained when the amide group is hydrolyzed, travoprost, travoprost acid, latanoprost, latanoprost acid, latanoprostene, tafluprost, tafluprost acid, etc., a prostaglandin EP2 agonist, a prostaglandin EP3 agonist, a nitric oxide donating prostaglandin compound such as latanoprostene bunod, or a combination thereof.

Any suitable amount of a prostaglandin compound, such as bimatoprost, bimatoprost acid, travoprost, travoprost acid, latanoprost, latanoprost acid, latanoprostene, tafluprost, tafluprost acid, etc., a prostaglandin EP2 agonist, or a prostaglandin EP3 agonist, may be used in the drug delivery system. For example, a drug delivery system may contain about 0.01-1 µg, about 1-2 µg, about 2-3 µg, about 3-4 µg, about 4-5 µg, about 5-6 µg, about 6-7 µg, about 7-8 µg, about 8-9 µg, about 9-10 µg, about 0.01-3 µg, about 3-6 µg, about 6-10 µg, about 0.01-10 µg, about 10-20 µg, about 20-30 µg, about 30-40 µg, about 40-50 µg, about 50-60 µg, about 60-70 µg, about 70-80 µg, about 80-90 µg, about 90-100 µg, about 0.010-30 µg, about 30-60 µg, about 60-100 µg, about 0.01-100 µg, about 0.010-100 µg, about 100-200 µg, about 200-300 µg, about 300-400 µg, about 400-500 µg, about 500-600 µg, about 600-700 µg, about 700-800 µg, about 800-900 µg, about 900-1,000 µg, about 0.01-300 µg, about 300-600 µg, about 600-1,000 µg, about 0.001-1 mg, 0.01-1 mg, about 0.1-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component. For example, a compound of Formula 1 or Formula 3 may be said to contain 1 mg of the prostaglandin compound even though the prostaglandin is covalently bound to other parts of the drug delivery system.

Use of the amounts given above for a prostaglandin compound, such as bimatoprost, bimatoprost acid, travoprost, travoprost acid, latanoprost, latanoprost acid, latanoprostene, tafluprost, tafluprost acid, etc., a prostaglandin EP2 agonist, or a prostaglandin EP3 agonist, in a drug delivery system, may provide a drug delivery system that provides therapeutic levels of the prostaglandin compound for about 1-4 weeks, about 1-3 months, about 3-6 months, about 6-9 months, about 9-12 months, about 12-18 months, about 18-24 months, about 2-5 years, about 5-10 years, or longer.

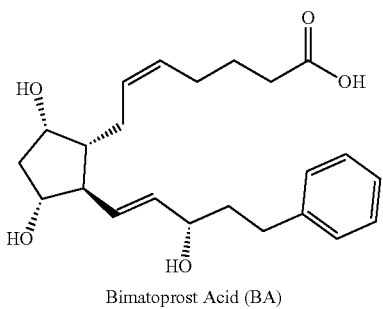 [SMILES: O=C(O)CCC/C=C\C[C@@H]1[C@@H](/C=C/[C@@H](O)CCc2ccccc2)[C@H](O)C[C@@H]1O]

Bimatoprost Acid (BA)

In some embodiments, the prostaglandin receptor agonist, prostanoid receptor agonist, or prostaglandin compound is bimatoprost (amide) or the bimatoprost acid. In some embodiments, the prostaglandin receptor agonist or prostaglandin compound is travoprost. In some embodiments, the prostaglandin receptor agonist or prostaglandin compound is travoprost acid. In some embodiments, the prostaglandin receptor agonist or prostaglandin compound is latanoprost. In some embodiments, the prostaglandin receptor agonist or prostaglandin compound is latanoprost acid. In some embodiments, the prostaglandin receptor agonist or prostaglandin compound is latanoprostene. In some embodiments, the prostaglandin receptor agonist or prostaglandin compound is tafluprost. In some embodiments, the prostaglandin receptor agonist or prostaglandin compound is tafluprost acid. In some embodiments, the prostaglandin receptor agonist or prostaglandin compound is a prostaglandin EP2 receptor agonist. In some embodiments, the prostaglandin receptor agonist or prostaglandin compound is a prostaglandin EP3 receptor agonist.

Some subject drug delivery systems may include an intraocular pressure lowering agent, such as a beta blocker, an alpha agonist, a carbonic anhydrase inhibitor, a Rho Kinase inhibitor, a cannabinoid receptor agonist, etc. Some subject drug delivery systems may include two or more intraocular pressure lowering agents, such as a prostaglandin compound, a prostaglandin receptor agonist, or a prostanoid receptor agonist; a beta blocker; an alpha agonist; a carbonic anhydrase inhibitor; a cannabinoid receptor agonist; a Rho kinase inhibitor; etc. Some subject drug delivery systems contain two or more of: a prostaglandin receptor agonist (or a prostaglandin compound or prostanoid receptor agonist), a beta blocker, an alpha agonist, a carbonic anhydrase inhibitor, a cannabinoid receptor agonist, a Rho kinase inhibitor, etc.

With respect to a subject drug delivery system, any suitable beta blocker, or any suitable beta adrenergic antagonist, may be used. Examples include timolol, betaxolol, levobunolol, metipranolol, etc., or a combination thereof. In some embodiments, the beta blocker is timolol. In some embodiments, the beta blocker is betaxolol. In some embodiments, the beta blocker is levobunolol. In some embodiments, the beta blocker is metipranolol.

Any suitable amount of a beta blocker or a beta adrenergic antagonist, such as timolol, betaxolol, levobunolol, or metipranolol, may be used in the drug delivery system. For example, a drug delivery system may contain about 0.01-1 μg, about 1-2 μg, about 2-3 μg, about 3-4 μg, about 4-5 μg, about 5-6 μg, about 6-7 μg, about 7-8 μg, about 8-9 μg, about 9-10 μg, about 0.01-3 μg, about 3-6 μg, about 6-10 μg, about 0.01-10 μg, about 10-20 μg, about 20-30 μg, about 30-40 μg, about 40-50 μg, about 50-60 μg, about 60-70 μg, about 70-80 μg, about 80-90 μg, about 90-100 μg, about 0.01-30 μg, about 30-60 μg, about 60-100 μg, about 0.01-100 μg, about 0.01-100 μg, about 100-200 μg, about 200-300 μg, about 300-400 μg, about 400-500 μg, about 500-600 μg, about 600-700 μg, about 700-800 μg, about 800-900 μg, about 900-1,000 μg, about 0.01-300 μg, about 300-600 μg, about 600-1,000 μg, about 0.001-1 mg, 0.01-1 mg, about 0.1-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for a beta blocker or a beta adrenergic antagonist, such as timolol, betaxolol, levobunolol, or metipranolol, in a drug delivery system, may provide a drug delivery system that provides therapeutic levels of the beta blocker or the beta adrenergic antagonist for about 1-4 weeks, about 1-3 months, about 3-6 months, about 6-9 months, about 9-12 months, about 12-18 months, about 18-24 months, about 2-5 years, about 5-10 years, or longer.

With respect to a subject drug delivery system, any suitable alpha agonist, or alpha adrenergic agonist, may be used. Examples include brimonidine, apraclonidine, etc., or a combination thereof. In some embodiments, the alpha agonist is brimonidine. In some embodiments, the alpha agonist is apraclonidine.

Any suitable amount of an alpha agonist or an alpha adrenergic agonist such as brimonidine, apraclonidine, etc., may be used in the drug delivery system. For example, a drug delivery system may contain about 0.01-1 μg, about 1-2 μg, about 2-3 μg, about 3-4 μg, about 4-5 μg, about 5-6 μg, about 6-7 μg, about 7-8 μg, about 8-9 μg, about 9-10 μg, about 0.01-3 μg, about 3-6 μg, about 6-10 μg, about 0.01-10 μg, about 10-20 μg, about 20-30 μg, about 30-40 μg, about 40-50 μg, about 50-60 μg, about 60-70 μg, about 70-80 μg, about 80-90 μg, about 90-100 μg, about 0.01-30 μg, about 30-60 μg, about 60-100 μg, about 0.01-100 μg, about 0.1-100 μg, about 100-200 μg, about 200-300 μg, about 300-400 μg, about 400-500 μg, about 500-600 μg, about 600-700 μg, about 700-800 μg, about 800-900 μg, about 900-1,000 μg, about 0.01-300 μg, about 300-600 μg, about 600-1,000 μg, about 0.001-1 mg, 0.01-1 mg, about 0.1-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for an alpha agonist or an alpha adrenergic agonist such as brimonidine, apraclonidine, etc., in a drug delivery system, may provide a drug delivery system that provides therapeutic levels of the alpha agonist or the alpha adrenergic agonist for about 1-4 weeks, about 1-3 months, about 3-6 months, about 6-9 months, about 9-12 months, about 12-18 months, about 18-24 months, about 2-5 years, about 5-10 years, or longer.

With respect to a subject drug delivery system, any suitable carbonic anhydrase inhibitor may be used. Examples include brinzolamide, acetazolamide, dorzolamide, methazolamide, etc., or a combination thereof. In some embodiments, the carbonic anhydrase inhibitor is brinzolamide. In some embodiments, the carbonic anhydrase inhibitor is acetazolamide. In some embodiments, the carbonic anhydrase inhibitor is dorzolamide. In some embodiments, the carbonic anhydrase inhibitor is methazolamide.

Any suitable amount of a carbonic anhydrase inhibitor such as brinzolamide, acetazolamide, dorzolamide, methazolamide, etc., may be used in the drug delivery system. For example, a drug delivery system may contain about 0.01-1 µg, about 1-2 µg, about 2-3 µg, about 3-4 µg, about 4-5 µg, about 5-6 µg, about 6-7 µg, about 7-8 µg, about 8-9 µg, about 9-10 µg, about 0.01-3 µg, about 3-6 µg, about 6-10 µg, about 0.01-10 µg, about 10-20 µg, about 20-30 µg, about 30-40 µg, about 40-50 µg, about 50-60 µg, about 60-70 µg, about 70-80 µg, about 80-90 µg, about 90-100 µg, about 0.01-30 µg, about 30-60 µg, about 60-100 µg, about 0.01-100 µg, about 0.1-100 µg, about 100-200 µg, about 200-300 µg, about 300-400 µg, about 400-500 µg, about 500-600 µg, about 600-700 µg, about 700-800 µg, about 800-900 µg, about 900-1,000 µg, about 0.01-300 µg, about 300-600 µg, about 600-1,000 µg, about 0.001-1 mg, 0.01-1 mg, about 0.1-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for a carbonic anhydrase inhibitor such as brinzolamide, acetazolamide, dorzolamide, methazolamide, etc., in a drug delivery system, may provide a drug delivery system that provides therapeutic levels of the carbonic anhydrase inhibitor for about 1-4 weeks, about 1-3 months, about 3-6 months, about 6-9 months, about 9-12 months, about 12-18 months, about 18-24 months, about 2-5 years, about 5-10 years, or longer.

With respect to a subject drug delivery system, any suitable cholinergic may be used. Examples include pilocarpine, carbachol, etc., or a combination thereof. In some embodiments, the cholinergic may be pilocarpine. In some embodiments, the cholinergic may be carbachol.

Any suitable amount of a cholinergic, such as pilocarpine, carbachol, etc., may be used in the drug delivery system. For example, a drug delivery system may contain about 0.01-1 µg, about 1-2 µg, about 2-3 µg, about 3-4 µg, about 4-5 µg, about 5-6 µg, about 6-7 µg, about 7-8 µg, about 8-9 µg, about 9-10 µg, about 0.01-3 µg, about 3-6 µg, about 6-10 µg, about 0.01-10 µg, about 10-20 µg, about 20-30 µg, about 30-40 µg, about 40-50 µg, about 50-60 µg, about 60-70 µg, about 70-80 µg, about 80-90 µg, about 90-100 µg, about 0.01-30 µg, about 30-60 µg, about 60-100 µg, about 0.01-100 µg, about 0.1-100 µg, about 100-200 µg, about 200-300 µg, about 300-400 µg, about 400-500 µg, about 500-600 µg, about 600-700 µg, about 700-800 µg, about 800-900 µg, about 900-1,000 µg, about 0.01-300 µg, about 300-600 µg, about 600-1,000 µg, about 0.001-1 mg, 0.01-1 mg, about 0.1-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for a cholinergic, such as pilocarpine, carbachol, etc., in a drug delivery system, may provide a drug delivery system that provides therapeutic levels of the cholinergic for about 1-4 weeks, about 1-3 months, about 3-6 months, about 6-9 months, about 9-12 months, about 12-18 months, about 18-24 months, about 2-5 years, about 5-10 years, or longer.

With respect to a subject drug delivery system, any suitable Rho kinase inhibitor, such as netarsudil, may be used. In some embodiments, the Rho kinase inhibitor is netarsudil.

Any suitable amount of a Rho kinase inhibitor, such as netarsudil, may be used in the drug delivery system. For example, a drug delivery system may contain about 0.01-1 µg, about 1-2 µg, about 2-3 µg, about 3-4 µg, about 4-5 µg, about 5-6 µg, about 6-7 µg, about 7-8 µg, about 8-9 µg, about 9-10 µg, about 0.01-3 µg, about 3-6 µg, about 6-10 µg, about 0.01-10 µg, about 10-20 µg, about 20-30 µg, about 30-40 µg, about 40-50 µg, about 50-60 µg, about 60-70 µg, about 70-80 µg, about 80-90 µg, about 90-100 µg, about 0.01-30 µg, about 30-60 µg, about 60-100 µg, about 0.01-100 µg, about 0.1-100 µg, about 100-200 µg, about 200-300 µg, about 300-400 µg, about 400-500 µg, about 500-600 µg, about 600-700 µg, about 700-800 µg, about 800-900 µg, about 900-1,000 µg, about 0.01-300 µg, about 300-600 µg, about 600-1,000 µg, about 0.001-1 mg, 0.01-1 mg, about 0.1-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for a Rho kinase inhibitor, such as netarsudil, in a drug delivery system, may provide a drug delivery system that provides therapeutic levels of the Rho kinase inhibitor for about 1-4 weeks, about 1-3 months, about 3-6 months, about 6-9 months, about 9-12 months, about 12-18 months, about 18-24 months, about 2-5 years, about 5-10 years, or longer.

With respect to a subject drug delivery system, any suitable Tie-2 agonist may be used, such as angiopoietin-1, angiopoietin-2, angiopoietin-3, angiopoietin-4, etc.

Any suitable amount of a Tie-2 agonist, such as angiopoietin-1, angiopoietin-2, angiopoietin-3, angiopoietin-4, etc., may be used in the drug delivery system. For example, a drug delivery system may contain about 0.01-1 µg, about 1-2 µg, about 2-3 µg, about 3-4 µg, about 4-5 µg, about 5-6 µg, about 6-7 µg, about 7-8 µg, about 8-9 µg, about 9-10 µg, about 0.01-3 µg, about 3-6 µg, about 6-10 µg, about 0.01-10 µg, about 10-20 µg, about 20-30 µg, about 30-40 µg, about 40-50 µg, about 50-60 µg, about 60-70 µg, about 70-80 µg, about 80-90 µg, about 90-100 µg, about 0.01-30 µg, about 30-60 µg, about 60-100 µg, about 0.01-100 µg, about 0.1-100 µg, about 100-200 µg, about 200-300 µg, about 300-400 µg, about 400-500 µg, about 500-600 µg, about 600-700 µg, about 700-800 µg, about 800-900 µg, about 900-1,000 µg, about 0.0100-300 µg, about 300-600 µg, about 600-1,000 µg, about 0.001-1 mg, 0.01-1 mg, about 0.1-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for Tie-2 agonist, such as angiopoietin-1, angiopoietin-2, angiopoietin-3, angiopoietin-4, etc., in a drug delivery system, may provide a drug delivery system that provides therapeutic levels of the Tie-2 agonist for about 1-4 weeks, about 1-3 months, about 3-6 months, about 6-9 months, about 9-12 months, about 12-18 months, about 18-24 months, about 2-5 years, about 5-10 years, or longer.

With respect to a subject drug delivery system, a neurotrophic agent can include a CNTF compound or another neurotrophic agent, a CNTF compound includes any compound having a structure or activity similar to Ciliary neurotrophic factor (CNTF), including CNTF, protein derivatives of CNTF, or a CNTF peptide. Examples include CNTF, a peptide containing part of the CNTF sequence, such as a neurotrophic peptide containing the sequence DGGL (SEQ ID NO: 20), e.g. Peptide 6 (P6; Ac-VGDG-GLFEKKL-NH2 (SEQ ID NO: 1)) and Peptide 21 (P21; Ac-DGGL$^A$G-NH2 (SEQ ID NO: 2)), recombinant CNTF (rhCNTF), or a neurotrophic peptide identified in U.S. Pat. No. 8,592,374, which is incorporated herein by reference for its disclosure related to neurotrophic peptides, including neurotrophic peptides having an adamantly group at the C- and/or N-terminal end, or any other peptide having similar biological activity to CNTF. Other neurotrophic agents include nerve growth factor (NGF), Brain-derived neurotrophic factor (BDNF), glial cell-derived neurotrophic factor (GDNF), etc.

Any suitable amount of a neurotrophic agent, such as a CNTF compound, NGF, BDNF, GDNF, etc., may be used in the drug delivery system. For example, a drug delivery system may contain about 0.01-1 µg, about 1-2 µg, about 2-3 µg, about 3-4 µg, about 4-5 µg, about 5-6 µg, about 6-7 µg, about 7-8 µg, about 8-9 µg, about 9-10 µg, about 0.01-3 µg, about 3-6 µg, about 6-10 µg, about 0.01-10 µg, about 10-20 µg, about 20-30 µg, about 30-40 µg, about 40-50 µg, about 50-60 µg, about 60-70 µg, about 70-80 µg, about 80-90 µg, about 90-100 µg, about 0.01-30 µg, about 30-60 µg, about 60-100 µg, about 0.01-100 µg, about 0.1-100 µg, about 100-200 µg, about 200-300 µg, about 300-400 µg, about 400-500 µg, about 500-600 µg, about 600-700 µg, about 700-800 µg, about 800-900 µg, about 900-1,000 µg, about 0.01-300 µg, about 300-600 µg, about 600-1,000 µg, about 0.001-1 mg, 0.01-1 mg, about 0.1-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for a neurotrophic agent, such as a CNTF compound, NGF, BDNF, GDNF, etc., in a drug delivery system, may provide a drug delivery system that provides therapeutic levels of the neurotrophic agent for about 1-4 weeks, about 1-3 months, about 3-6 months, about 6-9 months, about 9-12 months, about 12-18 months, about 18-24 months, about 2-5 years, about 5-10 years, or longer.

With respect to a subject drug delivery system, a CNP compound includes any compound having a structure or activity similar to C-type Natriuretic Peptide, including natural C-type Natriuretic Peptide.

Any suitable amount of a CNP compound, such as natural CNP, may be used in the drug delivery system. For example, a drug delivery system may contain about 0.01-1 µg, about 1-2 µg, about 2-3 µg, about 3-4 µg, about 4-5 µg, about 5-6 µg, about 6-7 µg, about 7-8 µg, about 8-9 µg, about 9-10 µg, about 0.01-3 µg, about 3-6 µg, about 6-10 µg, about 0.01-10 µg, about 10-20 µg, about 20-30 µg, about 30-40 µg, about 40-50 µg, about 50-60 µg, about 60-70 µg, about 70-80 µg, about 80-90 µg, about 90-100 µg, about 0.01-30 µg, about 30-60 µg, about 60-100 µg, about 0.01-100 µg, about 0.1-100 µg, about 100-200 µg, about 200-300 µg, about 300-400 µg, about 400-500 µg, about 500-600 µg, about 600-700 µg, about 700-800 µg, about 800-900 µg, about 900-1,000 µg, about 0.01-300 µg, about 300-600 µg, about 600-1,000 µg, about 0.001-1 mg, 0.01-1 mg, about 0.1-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for a CNP compound, such as natural CNP, in a drug delivery system, may provide a drug delivery system that provides therapeutic levels of the CNP compound for about 1-4 weeks, about 1-3 months, about 3-6 months, about 6-9 months, about 9-12 months, about 12-18 months, about 18-24 months, about 2-5 years, about 5-10 years, or longer.

With respect to a subject drug delivery system, an NPR-B compound includes any compound having a structure or activity similar to Natriuretic Peptide Receptor-B, including natural Natriuretic Peptide Receptor-B.

Any suitable amount of an NPR-B compound, such as natural NPR-B, may be used in the drug delivery system. For example, a drug delivery system may contain about 0.01-1 µg, about 1-2 µg, about 2-3 µg, about 3-4 µg, about 4-5 µg, about 5-6 µg, about 6-7 µg, about 7-8 µg, about 8-9 µg, about 9-10 µg, about 0.01-3 µg, about 3-6 µg, about 6-10 µg, about 0.01-10 µg, about 10-20 µg, about 20-30 µg, about 30-40 µg, about 40-50 µg, about 50-60 µg, about 60-70 µg, about 70-80 µg, about 80-90 µg, about 90-100 µg, about 0.01-30 µg, about 30-60 µg, about 60-100 µg, about 0.01-100 µg, about 0.1-100 µg, about 100-200 µg, about 200-300 µg, about 300-400 µg, about 400-500 µg, about 500-600 µg, about 600-700 µg, about 700-800 µg, about 800-900 µg, about 900-1,000 µg, about 0.01-300 µg, about 300-600 µg, about 600-1,000 µg, about 0.001-1 mg, about 0.01-1 mg, about 0.1-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for a NPR-B compound, such as natural NPR-B, in a drug delivery system, may provide a drug delivery system that provides therapeutic levels of the NPR-B compound for about 1-4 weeks, about 1-3 months, about 3-6 months, about 6-9 months, about 9-12 months, about 12-18 months, about 18-24 months, about 2-5 years, about 5-10 years, or longer.

Useful FAS or FASL inhibitors include bicyclol, FLIP; MET12 (HHIYLGAVNYIY (SEQ ID NO: 3), HHIYL-GATNYIY (SEQ ID NO: 4), or H$^{60}$HIYLGATNYIY$^{71}$ (SEQ ID NO: 4)), or a shorter fragment thereof, such as a tetramer having a sequence YLGA (SEQ ID NO: 5), or a fragment having a sequence homology of at least about 10%, at least about 20%, at least about 30%, at least about 40%, at least about 50%, at least about 60%, at least about 70%, at least about 80%, or at least about 90% sequence homology to MET12, including compound having a sequence shown in Table 1 below, such as compound 1, compound 2, compound 3, compound 4, compound 5, compound 6, compound 7, compound 8, compound 9, compound 10, or compound 11, MET4-8 (YLGA (SEQ ID NO: 5)), YLGAV (SEQ ID NO: 7), IYLGA (SEQ ID NO: 6), HIYLGA (SEQ ID NO: 8), IYLGAV (SEQ ID NO: 9), YLGAVN (SEQ ID NO: 16), IYLGAVN (SEQ ID NO: 11), HIYLGAV (SEQ ID NO: 10), or HIYLGAVN (SEQ ID NO: 17), MET4 (YLGA (SEQ ID NO: 5)), MET5 (YLGAV (SEQ ID NO: 7) and/or IYLGA (SEQ ID NO: 6)), MET6 (HIYLGA (SEQ ID NO: 8), IYLGAV (SEQ ID NO: 9), YLGAVN (SEQ ID NO: 16), and/or IYLGAVN (SEQ ID NO: 11)), MET7 (IYLGAVN (SEQ ID NO: 11) and/or HIYLGAV (SEQ ID NO: 10)), MET8 (HIYLGAVN (SEQ ID NO: 17)), (ONL1204 (e.g. a peptide comprising or consisting of a sequence HHIYLGATNYIY (SEQ ID NO: 4)); other MET12 derivatives such as a compound having a sequence: $H^{60}$HIYLGATNYIY$^{71}$-NH$_2$ (SEQ ID NO: 4), FAS apoptotic inhibitory molecule [FAIM]; NOL3 [nucleolar protein 3 (apoptosis repressor with CARD domain [ARC]), etc.]; DcR1; DcR2; or DcR3.

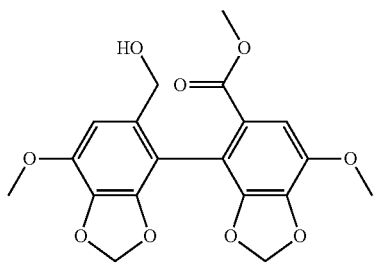

Bicyclol (BC)

TABLE 1

| Compound | Sequence | SEQ ID NO: |
|---|---|---|
| 1 | YLGA | 5 |
| 2 | IYLGA | 6 |
| 3 | YLGAV | 7 |
| 4 | HIYLGA | 8 |
| 5 | IYLGAV | 9 |
| 6 | HIYLGAV | 10 |
| 7 | IYLGAVN | 11 |
| 8 | HHIYLGA | 12 |
| 9 | YLGAVNY | 13 |
| 10 | HHIYLGAV | 14 |
| 11 | YLGAVNYI | 15 |

Any suitable amount of a FAS or FASL inhibitor, such as bicyclol, FLIP, compound 1, compound 2, compound 3, compound 4, compound 5, compound 6, compound 7, compound 8, compound 9, compound 10, or compound 11, ONL1204, $H^{60}$HIYLGATNYIY$^{71}$-NH$_2$ (SEQ ID NO: 4), FAIM, NOL3, DcR1, DcR2, DcR3, etc., may be used in the drug delivery system. For example, a drug delivery system may contain about 0.01-1 µg, about 1-2 µg, about 2-3 µg, about 3-4 µg, about 4-5 µg, about 5-6 µg, about 6-7 µg, about 7-8 µg, about 8-9 µg, about 9-10 µg, about 0.01-3 µg, about 3-6 µg, about 6-10 µg, about 0.01-10 µg, about 10-20 µg, about 20-30 µg, about 30-40 µg, about 40-50 µg, about 50-60 µg, about 60-70 µg, about 70-80 µg, about 80-90 µg, about 90-100 µg, about 0.01-30 µg, about 30-60 µg, about 60-100 µg, about 0.01-100 µg, about 0.1-100 µg, about 100-200 µg, about 200-300 µg, about 300-400 µg, about 400-500 µg, about 500-600 µg, about 600-700 µg, about 700-800 µg, about 800-900 µg, about 900-1,000 µg, about 0.0100-300 µg, about 300-600 µg, about 600-1,000 µg, about 0.001-1 mg, 0.01-1 mg, about 0.1-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for a FAS or FASL inhibitor, such as bicyclol, FLIP, compound 1, compound 2, compound 3, compound 4, compound 5, compound 6, compound 7, compound 8, compound 9, compound 10, or compound 11, ONL1204, $H^{60}$HIYLGATNYIY$^{71}$-NH$_2$ (SEQ ID NO: 4), FAIM, NOL3, DcR1, DcR2, DcR3, etc., in a drug delivery system, may provide a drug delivery system that provides therapeutic levels of the NPR-B compound for about 1-4 weeks, about 1-3 months, about 3-6 months, about 6-9 months, about 9-12 months, about 12-18 months, about 18-24 months, about 2-5 years, about 5-10 years, or longer.

Table 2 below depicts drug combinations that are of particular interest in a subject drug delivery system.

TABLE 2

| Drug 1 | Drug 2 |
|---|---|
| PG | beta blocker |
| PG | alpha agonist |
| PG | carbonic anhydrase inhibitor |
| PG | Rho Kinase inhibitor |
| beta blocker | alpha agonist |
| beta blocker | carbonic anhydrase inhibitor |
| beta blocker | Rho Kinase inhibitor |
| alpha agonist | carbonic anhydrase inhibitor |
| alpha agonist | Rho Kinase inhibitor |
| carbonic anhydrase inhibitor | Rho Kinase inhibitor |
| intraocular pressure lowering agent | neurotrophic agent |
| intraocular pressure lowering agent | CNTF compound |
| intraocular pressure lowering agent | CNP compound |
| intraocular pressure lowering agent | NPR-B compound |
| CNTF compound | CNP compound |
| CNTF compound | NPR-B compound |
| CNTF compound | PG |
| CNTF compound | beta blocker |
| CNTF compound | alpha agonist |
| CNTF compound | carbonic anhydrase inhibitor |
| CNTF compound | Rho Kinase inhibitor |
| CNP compound | NPR-B compound |
| CNP compound | PG |
| CNP compound | beta blocker |
| CNP compound | alpha agonist |
| CNP compound | carbonic anhydrase inhibitor |
| CNP compound | Rho Kinase inhibitor |
| NPR-B compound | PG |
| NPR-B compound | beta blocker |
| NPR-B compound | alpha agonist |

TABLE 2-continued

| Drug 1 | Drug 2 |
| --- | --- |
| NPR-B compound | carbonic anhydrase inhibitor |
| NPR-B compound | Rho Kinase inhibitor |
| Tie-2 agonist | PG |
| Tie-2 agonist | beta blocker |
| Tie-2 agonist | alpha agonist |
| Tie-2 agonist | carbonic anhydrase inhibitor |
| Tie-2 agonist | Rho Kinase inhibitor |
| Tie-2 agonist | cannabinoid receptor agonist |
| Tie-2 agonist | CNTF compound |
| Tie-2 agonist | CNP compound |
| Tie-2 agonist | NPR-B compound |
| Cannabinoid receptor agonist | PG |
| Cannabinoid receptor agonist | beta blocker |
| Cannabinoid receptor agonist | alpha agonist |
| Cannabinoid receptor agonist | carbonic anhydrase inhibitor |
| Cannabinoid receptor agonist | Rho Kinase inhibitor |
| Cannabinoid receptor agonist | CNTF compound |
| Cannabinoid receptor agonist | CNP compound |
| Cannabinoid receptor agonist | NPR-B compound |
| Neurotrophic agent | CNP compound |
| Neurotrophic agent | NPR-B compound |
| Neurotrophic agent | PG |
| Neurotrophic agent | beta blocker |
| Neurotrophic agent | alpha agonist |
| Neurotrophic agent | carbonic anhydrase inhibitor |
| Neurotrophic agent | Rho Kinase inhibitor |
| FAS or FASL inhibitor | PG |
| FAS or FASL inhibitor | beta blocker |
| FAS or FASL inhibitor | alpha agonist |
| FAS or FASL inhibitor | carbonic anhydrase inhibitor |
| FAS or FASL inhibitor | Rho Kinase inhibitor |
| FAS or FASL inhibitor | cannabinoid receptor agonist |
| FAS or FASL inhibitor | CNTF compound |
| FAS or FASL inhibitor | CNP compound |
| FAS or FASL inhibitor | NPR-B compound |
| FAS or FASL inhibitor | Tie-2 agonist |

PG: prostaglandin compound or prostaglandin receptor agonist, including acid, salt, and ester or ester prodrug forms Some drug delivery systems include a combination of bimatoprost acid and bicyclol, which is either directly covalently bonded, bonded with a linking group, or wherein both are bonded to a polymer or to a silicon-based drug delivery particle.

With respect to a subject drug delivery system comprising a prostaglandin receptor agonist or a prostaglandin compound and an intraocular pressure lowering agent, in some embodiments, the prostaglandin receptor agonist is covalently bound to the intraocular pressure lowering agent. In some embodiments, the prostaglandin receptor agonist is covalently bound to the intraocular pressure lowering agent via a linking group.

For example, some compounds containing a prostaglandin compound or a prostaglandin receptor agonist covalently bound to an intraocular pressure lowering agent by a linking group are represented by Formula 1 or 1A:

PG-L-IOP    Formula 1

IOP-L-IOP    Formula 1A wherein PG-H or PG-OH is a prostaglandin receptor agonist, such as a prostaglandin compound or prostaglandin receptor agonist recited above; and each IOP-H or IOP-OH is independently an intraocular pressure lowering agent, such as an intraocular pressure lowering agent recited above.

With respect to a subject drug delivery system comprising both the prostaglandin receptor agonist and the neurotrophic agent, such as the CNTF compound, in some embodiments, the prostaglandin receptor agonist and the neurotrophic agent, such as the CNTF compound, are covalently bound to one another. In some embodiments, the prostaglandin receptor agonist and the neurotrophic agent, such as the CNTF compound, are covalently bound to one another via a linking group.

Some subject drug delivery systems comprise both the intraocular pressure lowering agent and the neurotrophic agent, such as the CNTF compound. In some embodiments, the intraocular pressure lowering agent and the neurotrophic agent, such as the CNTF compound, are covalently bound to one another. In some embodiments, the intraocular pressure lowering agent and the neurotrophic agent, such as the CNTF compound, are covalently bound to one another via a linking group.

Some subject drug delivery systems comprise both the intraocular pressure lowering agent and the CNP compound. In some embodiments, the intraocular pressure lowering agent and the CNP compound are covalently bound to one another. In some embodiments, the intraocular pressure lowering agent and the CNP compound are covalently bound to one another via a linking group.

Some subject drug delivery systems comprise the intraocular pressure lowering agent and the NPR-B compound. In some embodiments, the intraocular pressure lowering agent and the NPR-B compound are covalently bound to one another. In some embodiments, the intraocular pressure lowering agent and the NPR-B compound are covalently bound to one another via a linking group.

Some subject drug delivery systems comprise both the neurotrophic agent, such as the CNTF compound, and the CNP compound. In some embodiments, the neurotrophic agent, such as the CNTF compound, and the CNP compound are covalently bound to one another. In some embodiments, the neurotrophic agent, such as the CNTF compound, and the CNP compound are covalently bound to one another via a linking group.

Some subject drug delivery systems comprise both the neurotrophic agent, such as the CNTF compound, and the NPR-B compound. In some embodiments, the neurotrophic agent, such as the CNTF compound, and the NPR-B compound are covalently bound to one another. In some embodiments, the neurotrophic agent, such as the CNTF compound, and the NPR-B compound are covalently bound to one another via a linking group.

Some subject drug delivery systems comprise both and the CNP compound and the NPR-B compound. In some embodiments, the CNP compound and the NPR-B compound are covalently bound to one another. In some embodiments, the CNP compound and the NPR-B compound are covalently bound to one another via a linking group.

For example, some compounds containing a prostaglandin compound or a prostaglandin receptor covalently bound to a CNTF compound by a linking group are represented by Formula 2:

PG-L-CNTF    Formula 2 wherein PG-H or PG-OH is a prostaglandin receptor agonist, such as a prostaglandin compound or prostaglandin receptor agonist recited above; and CNTF-H or CNTF-OH is a CNTF compound, such as a CNTF compound recited above.

Other covalently linked compounds include compounds represented by Formula 2A, 2B, 2C, 2D, 2E, or 2F:

IOP-L-CNTF    Formula 2A

IOP-L-CNP    Formula 2B

IOP-L-NPRB    Formula 2C

| | |
|---|---|
| CNTF-L-CNP | Formula 2D |
| CNTF-L-NPRB | Formula 2E |
| CNP-L-NPRB | Formula 2F |

Wherein IOP-H is intraocular pressure lowering agent, such as an intraocular pressure lowering agent recited above; CNTF-H or CNTF-OH is a CNTF compound, such as a CNTF compound recited above; CNP-H or CNP-OH is a CNP compound; and NPR-H or NPR-OH is an NPR-B compound.

With respect to any relevant structural representation, such as Formula 1, 2, 2A, 2B, 2C, 2D, 2E, 2F, 3, 4, 5, 3D, 4D, or 5D (Formulas 3-5 and 3D-5D are depicted below), L is a linking group represented by the empirical formula $C_aH_bO_cN_d$ or $C_aH_bO_c$.

With respect to any L, a is 1, 2, 3, 4, 5, 6, 7, 8, 9, 10, 11, 12, 13, 14, 15, 16, 17, 18, 19, or 20. In some embodiments, a is 1-5, 5-10, 10-15, 15-20, 1-10, or 10-20.

With respect to any L, b is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43. In some embodiments, b is 1-10, 10-20, 20-30, 30-40, 40-43, 1-15, 15-30, or 30-43.

With respect to any L, c is 0, 1, 2, 3, 4, 5, 6, 7, 8, 9, or 10. In some embodiments, c is 0-2, 2-4, 4-6, 6-8, 8-10, 0-3, 3-6, or 6-10.

With respect to any L, d is 0, 1, or 2. In some embodiments, d is 0. In some embodiments, d is 1. In some embodiments, d is 2.

In some embodiments, L may be represented by Formula L-1, L-2, L-3, L-4, L-5, L-6, L-7, or L-8:

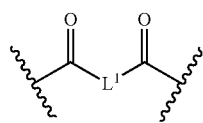

Formula L-1

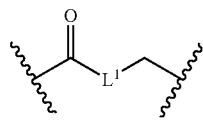

Formula L-2

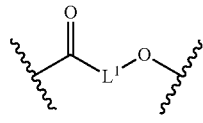

Formula L-3

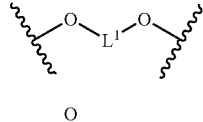

Formula L-4

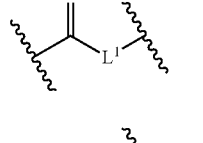

Formula L-5

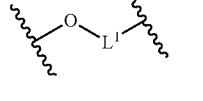

Formula L-6

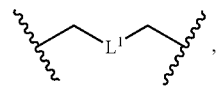

Formula L-7

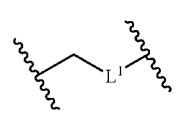

Formula L-8

With respect to any relevant structural representation, such as Formula L-1, L-2, L-3, L-4, L-5, L-6, L-7, or L-8, $L^1$ may be represented by the empirical formula $C_eH_fO_gN_h$ or $C_eH_fO_g$.

With respect to any $L^1$, e is 1, 2, 3, 4, 5, 6, 7, 8, 9, 10, 11, 12, 13, 14, 15, 16, 17, or 18. In some embodiments, e is 1-5, 5-10, 10-15, 15-18, 1-10, or 10-18.

With respect to any $L^1$, f is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38. In some embodiments, f is 1-10, 10-20, 20-30, 30-38, 1-15, 15-30, or 30-38.

With respect to any $L^1$, g is 0, 1, 2, 3, 4, 5, 6, 7, or 8. In some embodiments, g is 0-2, 2-4, 4-6, 6-8, 0-3, 3-6, or 6-8.

With respect to any $L^1$, h is 0, 1, or 2. In some embodiments, h is 0. In some embodiments, h is 1. In some embodiments, h is 2.

With respect to any relevant structural representation, such as Formula L-1, L-2, L-3, L-4, L-5, L-6, L-7, or L-8, in some embodiments $L^1$ may be:

$$—(CH_2)_i—(OCH_2CH_2)_j—O—(CH_2)_k— \quad [\text{Formula } L^1\text{-1}],$$

$$—(CH_2)_i—(OCH_2CH_2)_j—O—CONH—(CH_2)_k— \quad [\text{Formula } L^1\text{-2}],$$

$$—(C_iH_{2i})—(OCH_2CH_2)_j—O—(C_kH_{2k})— \quad [\text{Formula } L^1\text{-3}],$$

$$—(C_iH_{2i})—(OCH_2CH_2)_j—O—CONH—(C_kH_{2k})— \quad [\text{Formula } L^1\text{-4}],$$

$$—NH_2(CH_2)_i—(OCH_2CH_2)_j—O—(CH_2)_k— \quad [\text{Formula } L^1\text{-5}],$$

$$—NH_2(CH_2)_i—(OCH_2CH_2)_j—O—CONH—(CH_2)_k— \quad [\text{Formula } L^1\text{-6}],$$

$$—NH_2(C_iH_{2i})—(OCH_2CH_2)_j—O—(C_kH_{2k})— \quad [\text{Formula } L^1\text{-7}], \text{ or}$$

$$—NH_2(C_iH_{2i})—(OCH_2CH_2)_j—O—CONH—(C_kH_{2k})— \quad [\text{Formula } L^1\text{-8}].$$

With respect to any relevant structural representation, such as Formula $L^1$-1, $L^1$-2, $L^1$-3, $L^1$-4, $L^1$-5, $L^1$-6, $L^1$-7, or $L^1$-8, i is 0, 1, 2, 3, or 4. In some embodiments, i is 2.

With respect to any relevant structural representation, such as Formula $L^1$-1, $L^1$-2, $L^1$-3, $L^1$-4, $L^1$-5, $L^1$-6, $L^1$-7, or $L^1$-8, j is 0, 1, 2, 3, or 5.

With respect to any relevant structural representation, such as Formula $L^1$-1, $L^1$-2, $L^1$-3, $L^1$-4, $L^1$-5, $L^1$-6, $L^1$-7, or $L^1$-8, k is 0, 1, 2, 3, or 4.

With respect to Formula $L^1$-1, $L^1$-2, $L^1$-3, $L^1$-4, $L^1$-5, $L^1$-6, $L^1$-7, or $L^1$-8, any H atom of an NH or an $NH_2$ moiety may be replaced with a substituent, such as $C_{1-12}$ hydrocarbyl, $C_{1-6}$ hydrocarbyl, or $C_{1-3}$ hydrocarbyl group, including phenyl, $C_{1-12}$ alkyl, $C_{1-6}$ alkyl, $C_{3-12}$ cycloalkyl, $C_{3-6}$ cycloalkyl, $C_{1-3}$ alkyl, $C_{1-12}$ alkenyl, $C_{2-6}$ alkenyl, $C_{3-12}$ cycloalkenyl, $C_{3-6}$ cycloalkenyl, $C_{2-3}$ alkenyl, $C_{2-12}$ alkynyl, $C_{2-6}$ alkynyl, $C_{8-12}$ cycloalkynyl, $C_{2-3}$ alkynyl, etc.

In some embodiments, H-L-H, HO-L-H, HO-L-OH, H₂N-L-H, or H₂N-L-NH₂, or HO-L-NH₂ is one or more of the following:

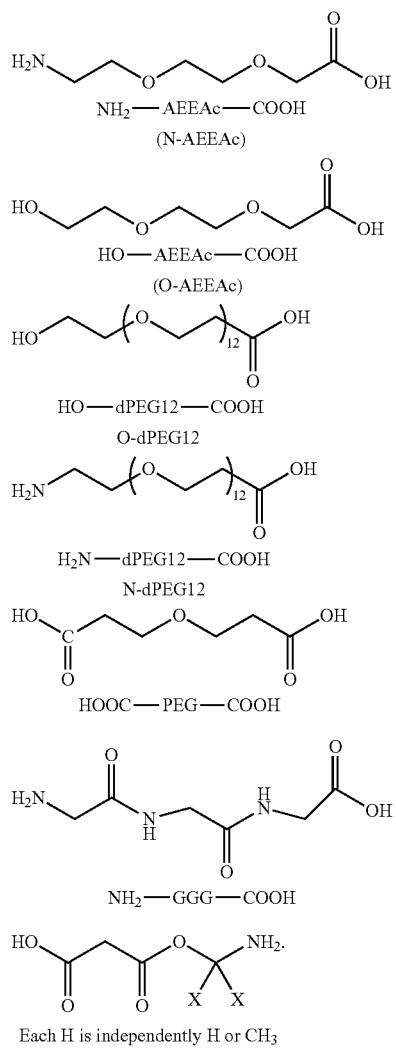

Compounds comprising linkers based upon O-AEEAC, O-dPEG12, LaL1, or LaL2 may be labile in a mammal body or a human body.

In some embodiments; a drug delivery system comprises one of the following drug combinations; including salts; free acids; or free based of the drugs; either covalently linked (such as by a linking group L, including groups represented by Formula L-1, L-2, L-3, L-4, L-5, L-6, L-7, or L-8 or not covalently linked: bimatoprost or bimatoprost acid and travoprost or travoprost acid; bimatoprost or bimatoprost acid and latanoprost or latanoprost acid; bimatoprost or bimatoprost acid and latanoprostene; bimatoprost or bimatoprost acid and tafluprost or tafluprost acid; bimatoprost or bimatoprost acid and timolol; bimatoprost or bimatoprost acid and betaxolol; bimatoprost or bimatoprost acid and levobunolol; bimatoprost or bimatoprost acid and metipranolol; bimatoprost or bimatoprost acid and brimonidine; bimatoprost or bimatoprost acid and apraclonidine; bimatoprost or bimatoprost acid and brinzolamide; bimatoprost or bimatoprost acid and acetazolamide; bimatoprost or bimatoprost acid and dorzolamide; bimatoprost or bimatoprost acid and methazolamide; bimatoprost or bimatoprost acid and pilocarpine; bimatoprost or bimatoprost acid and carbachol; bimatoprost or bimatoprost acid and netarsudil; bimatoprost or bimatoprost acid and angiopoietin-1; bimatoprost or bimatoprost acid and angiopoietin-2; bimatoprost or bimatoprost acid and angiopoietin-3; bimatoprost or bimatoprost acid and angiopoietin-4; bimatoprost or bimatoprost acid and CNTF; bimatoprost or bimatoprost acid and Peptide 6; bimatoprost or bimatoprost acid and Peptide 21; bimatoprost or bimatoprost acid and recombinant CNTF; bimatoprost or bimatoprost acid and NGF; bimatoprost or bimatoprost acid and BDNF; bimatoprost or bimatoprost acid and GDNF; bimatoprost or bimatoprost acid and C-type Natriuretic Peptide; bimatoprost or bimatoprost acid and natural C-type Natriuretic Peptide; bimatoprost or bimatoprost acid and Natriuretic Peptide Receptor-B; bimatoprost or bimatoprost acid and bicyclol; bimatoprost or bimatoprost acid and FLIP; bimatoprost or bimatoprost acid and MET12; bimatoprost or bimatoprost acid and compound 1 from Table 1; bimatoprost or bimatoprost acid and compound 2 from Table 1; bimatoprost or bimatoprost acid and compound 3 from Table 1; bimatoprost or bimatoprost acid and compound 4 from Table 1; bimatoprost or bimatoprost acid and compound 5 from Table 1; bimatoprost or bimatoprost acid and compound 6 from Table 1; bimatoprost or bimatoprost acid and compound 7 from Table 1; bimatoprost or bimatoprost acid and compound 8 from Table 1; bimatoprost or bimatoprost acid and compound 9 from Table 1; bimatoprost or bimatoprost acid and compound 10 from Table 1; bimatoprost or bimatoprost acid and compound 11 from Table 1; bimatoprost or bimatoprost acid and H⁶⁰HIYLGATNYIY⁷¹-NH₂ (SEQ ID NO: 4); bimatoprost or bimatoprost acid and FAIM; bimatoprost or bimatoprost acid and NOL3; bimatoprost or bimatoprost acid and DcR1; bimatoprost or bimatoprost acid and DcR2; bimatoprost or bimatoprost acid and DcR3; travoprost or travoprost acid and latanoprost or latanoprost acid; travoprost or travoprost acid and latanoprostene; travoprost or travoprost acid and tafluprost or tafluprost acid; travoprost or travoprost acid and timolol; travoprost or travoprost acid and betaxolol; travoprost or travoprost acid and levobunolol; travoprost or travoprost acid and metipranolol; travoprost or travoprost acid and brimonidine; travoprost or travoprost acid and apraclonidine; travoprost or travoprost acid and brinzolamide; travoprost or travoprost acid and acetazolamide; travoprost or travoprost acid and dorzolamide; travoprost or travoprost acid and methazolamide; travoprost or travoprost acid and pilocarpine; travoprost or travoprost acid and carbachol; travoprost or travoprost acid and netarsudil; travoprost or travoprost acid and angiopoietin-1; travoprost or travoprost acid and angiopoietin-2; travoprost or travoprost acid and angiopoietin-3; travoprost or travoprost acid and angiopoietin-4; travoprost or travoprost acid and CNTF; travoprost or travoprost acid and Peptide 6; travoprost or travoprost acid and Peptide 21; travoprost or travoprost acid and recombinant CNTF; travoprost or travoprost acid and NGF; travoprost or travoprost acid and BDNF; travoprost or travoprost acid and GDNF; travoprost or travoprost acid and C-type Natriuretic Peptide; travoprost or travoprost acid and natural C-type Natriuretic Peptide; travoprost or travoprost acid and Natriuretic Peptide Receptor-B; travoprost or travoprost acid and bicyclol; travoprost or travoprost acid and FLIP; travoprost or travoprost acid and MET12; travoprost or travoprost acid and compound 1 from Table 1; travoprost or travoprost acid and compound 2 from Table 1; travoprost or travoprost acid and compound 3 from Table 1; travoprost or travoprost acid and compound 4 from Table 1; travoprost or travoprost acid and compound 5 from Table 1; travoprost or travoprost acid and compound 6 from Table 1; travoprost or travoprost acid and compound 7 from Table 1; travoprost or travoprost acid and compound 8 from Table 1; travoprost or travoprost acid and compound 9 from Table 1; travoprost or travoprost acid and compound 10 from Table 1; travoprost or travoprost acid and compound 11 from Table 1; travoprost or travoprost acid and $H^{60}HIYLGATNYIY^{71}$-$NH_2$ (SEQ ID NO: 4); travoprost or travoprost acid and FAIM; travoprost or travoprost acid and NOL3; travoprost or travoprost acid and DcR1; travoprost or travoprost acid and DcR2; travoprost or travoprost acid and DcR3; latanoprost or latanoprost acid and latanoprostene; latanoprost or latanoprost acid and tafluprost or tafluprost acid; latanoprost or latanoprost acid and timolol; latanoprost or latanoprost acid and betaxolol; latanoprost or latanoprost acid and levobunolol; latanoprost or latanoprost acid and metipranolol; latanoprost or latanoprost acid and brimonidine; latanoprost or latanoprost acid and apraclonidine; latanoprost or latanoprost acid and brinzolamide; latanoprost or latanoprost acid and acetazolamide; latanoprost or latanoprost acid and dorzolamide; latanoprost or latanoprost acid and methazolamide; latanoprost or latanoprost acid and pilocarpine; latanoprost or latanoprost acid and carbachol; latanoprost or latanoprost acid and netarsudil; latanoprost or latanoprost acid and angiopoietin-1; latanoprost or latanoprost acid and angiopoietin-2; latanoprost or latanoprost acid and angiopoietin-3; latanoprost or latanoprost acid and angiopoietin-4; latanoprost or latanoprost acid and CNTF; latanoprost or latanoprost acid and Peptide 6; latanoprost or latanoprost acid and Peptide 21; latanoprost or latanoprost acid and recombinant CNTF; latanoprost or latanoprost acid and NGF; latanoprost or latanoprost acid and BDNF; latanoprost or latanoprost acid and GDNF; latanoprost or latanoprost acid and C-type Natriuretic Peptide; latanoprost or latanoprost acid and natural C-type Natriuretic Peptide; latanoprost or latanoprost acid and Natriuretic Peptide Receptor-B; latanoprost or latanoprost acid and bicyclol; latanoprost or latanoprost acid and FLIP; latanoprost or latanoprost acid and MET12; latanoprost or latanoprost acid and compound 1 from Table 1; latanoprost or latanoprost acid and compound 2 from Table 1; latanoprost or latanoprost acid and compound 3 from Table 1; latanoprost or latanoprost acid and compound 4 from Table 1; latanoprost or latanoprost acid and compound 5 from Table 1; latanoprost or latanoprost acid and compound 6 from Table 1; latanoprost or latanoprost acid and compound 7 from Table 1; latanoprost or latanoprost acid and compound 8 from Table 1; latanoprost or latanoprost acid and compound 9 from Table 1; latanoprost or latanoprost acid and compound 10 from Table 1; latanoprost or latanoprost acid and compound 11 from Table 1; latanoprost or latanoprost acid and $H^{60}HIYLGATNYIY^{71}$-$NH_2$ (SEQ ID NO: 4); latanoprost or latanoprost acid and FAIM; latanoprost or latanoprost acid and NOL3; latanoprost or latanoprost acid and DcR1; latanoprost or latanoprost acid and DcR2; latanoprost or latanoprost acid and DcR3; latanoprostene and tafluprost or tafluprost acid; latanoprostene and timolol; latanoprostene and betaxolol; latanoprostene and levobunolol; latanoprostene and metipranolol; latanoprostene and brimonidine; latanoprostene and apraclonidine; latanoprostene and brinzolamide; latanoprostene and acetazolamide; latanoprostene and dorzolamide; latanoprostene and methazolamide; latanoprostene and pilocarpine; latanoprostene and carbachol; latanoprostene and netarsudil; latanoprostene and angiopoietin-1; latanoprostene and angiopoietin-2; latanoprostene and angiopoietin-3; latanoprostene and angiopoietin-4; latanoprostene and CNTF; latanoprostene and Peptide 6; latanoprostene and Peptide 21; latanoprostene and recombinant CNTF; latanoprostene and NGF; latanoprostene and BDNF; latanoprostene and GDNF; latanoprostene and C-type Natriuretic Peptide; latanoprostene and natural C-type Natriuretic Peptide; latanoprostene and Natriuretic Peptide Receptor-B; latanoprostene and bicyclol; latanoprostene and FLIP; latanoprostene and MET12; latanoprostene and compound 1 from Table 1; latanoprostene and compound 2 from Table 1; latanoprostene and compound 3 from Table 1; latanoprostene and compound 4 from Table 1; latanoprostene and compound 5 from Table 1; latanoprostene and compound 6 from Table 1; latanoprostene and compound 7 from Table 1; latanoprostene and compound 8 from Table 1; latanoprostene and compound 9 from Table 1; latanoprostene and compound 10 from Table 1; latanoprostene and compound 11 from Table 1; latanoprostene and $H^{60}HIYLGATNYIY^{71}$-$NH_2$ (SEQ ID NO: 4); latanoprostene and FAIM; latanoprostene and NOL3; latanoprostene and DcR1; latanoprostene and DcR2; latanoprostene and DcR3; tafluprost or tafluprost acid and timolol; tafluprost or tafluprost acid and betaxolol; tafluprost or tafluprost acid and levobunolol; tafluprost or tafluprost acid and metipranolol; tafluprost or tafluprost acid and brimonidine; tafluprost or tafluprost acid and apraclonidine; tafluprost or tafluprost acid and brinzolamide; tafluprost or tafluprost acid and acetazolamide; tafluprost or tafluprost acid and dorzolamide; tafluprost or tafluprost acid and methazolamide; tafluprost or tafluprost acid and pilocarpine; tafluprost or tafluprost acid and carbachol; tafluprost or tafluprost acid and netarsudil; tafluprost or tafluprost acid and angiopoietin-1; tafluprost or tafluprost acid and angiopoietin-2; tafluprost or tafluprost acid and angiopoietin-3; tafluprost or tafluprost acid and angiopoietin-4; tafluprost or tafluprost acid and CNTF; tafluprost or tafluprost acid and Peptide 6; tafluprost or tafluprost acid and Peptide 21; tafluprost or tafluprost acid and recombinant CNTF; tafluprost or tafluprost acid and NGF; tafluprost or tafluprost acid and BDNF; tafluprost or tafluprost acid and GDNF; tafluprost or tafluprost acid and C-type Natriuretic Peptide; tafluprost or tafluprost acid and natural C-type Natriuretic Peptide; tafluprost or tafluprost acid and Natriuretic Peptide Receptor-B; tafluprost or tafluprost acid and bicyclol; tafluprost or tafluprost acid and FLIP; tafluprost or tafluprost acid and MET12; tafluprost or tafluprost acid and compound 1 from Table 1; tafluprost or tafluprost acid and compound 2 from Table 1; tafluprost or tafluprost acid and compound 3 from Table 1; tafluprost or tafluprost acid and compound 4 from Table 1; tafluprost or tafluprost acid and compound 5 from Table 1; tafluprost or tafluprost acid and compound 6 from Table 1; tafluprost or tafluprost acid and compound 7 from Table 1; tafluprost or tafluprost acid and compound 8 from Table 1; tafluprost or tafluprost acid and compound 9 from Table 1; tafluprost or tafluprost acid and compound 10 from Table 1; tafluprost or tafluprost acid and compound 11 from Table 1; tafluprost or tafluprost acid and $H^{60}HIYLGATNYIY^{71}$-$NH_2$ (SEQ ID NO: 4); tafluprost or tafluprost acid and FAIM; tafluprost or tafluprost acid and NOL3; tafluprost or tafluprost acid and DcR1; tafluprost or tafluprost acid and DcR2; tafluprost or tafluprost acid and DcR3; timolol and betaxolol; timolol and levobunolol; timolol and metipranolol; timolol and brimonidine; timolol and apraclonidine; timolol and brinzolamide; timolol and acetazolamide; timolol and dorzolamide; timolol and methazolamide; timolol and pilocarpine; timolol and carbachol; timolol and netarsudil; timolol and angiopoietin-1; timolol and angiopoietin-2; timolol and angiopoietin-3; timolol and angiopoietin-4; timolol and CNTF; timolol and Peptide 6; timolol and Peptide 21; timolol and recombinant CNTF; timolol and NGF; timolol and BDNF; timolol and GDNF; timolol and C-type Natriuretic Peptide; timolol and natural C-type Natriuretic Peptide; timolol and Natriuretic Peptide Receptor-B; timolol and bicyclol; timolol and FLIP; timolol and MET12; timolol and compound 1 from Table 1; timolol and compound 2 from Table 1; timolol and compound 3 from Table 1; timolol and compound 4 from Table 1; timolol and compound 5 from Table 1; timolol and compound 6 from Table 1; timolol and compound 7 from Table 1; timolol and compound 8 from Table 1; timolol and compound 9 from Table 1; timolol and compound 10 from Table 1; timolol and compound 11 from Table 1; timolol and H$^{60}$HIYLGATNYIY$^{71}$-NH$_2$ (SEQ ID NO: 4); timolol and FAIM; timolol and NOL3; timolol and DcR1; timolol and DcR2; timolol and DcR3; betaxolol and levobunolol; betaxolol and metipranolol; betaxolol and brimonidine; betaxolol and apraclonidine; betaxolol and brinzolamide; betaxolol and acetazolamide; betaxolol and dorzolamide; betaxolol and methazolamide; betaxolol and pilocarpine; betaxolol and carbachol; betaxolol and netarsudil; betaxolol and angiopoietin-1; betaxolol and angiopoietin-2; betaxolol and angiopoietin-3; betaxolol and angiopoietin-4; betaxolol and CNTF; betaxolol and Peptide 6; betaxolol and Peptide 21; betaxolol and recombinant CNTF; betaxolol and NGF; betaxolol and BDNF; betaxolol and GDNF; betaxolol and C-type Natriuretic Peptide; betaxolol and natural C-type Natriuretic Peptide; betaxolol and Natriuretic Peptide Receptor-B; betaxolol and bicyclol; betaxolol and FLIP; betaxolol and MET12; betaxolol and compound 1 from Table 1; betaxolol and compound 2 from Table 1; betaxolol and compound 3 from Table 1; betaxolol and compound 4 from Table 1; betaxolol and compound 5 from Table 1; betaxolol and compound 6 from Table 1; betaxolol and compound 7 from Table 1; betaxolol and compound 8 from Table 1; betaxolol and compound 9 from Table 1; betaxolol and compound 10 from Table 1; betaxolol and compound 11 from Table 1; betaxolol and H$^{60}$HIYLGATNYIY$^{71}$-NH$_2$ (SEQ ID NO: 4); betaxolol and FAIM; betaxolol and NOL3; betaxolol and DcR1; betaxolol and DcR2; betaxolol and DcR3; levobunolol and metipranolol; levobunolol and brimonidine; levobunolol and apraclonidine; levobunolol and brinzolamide; levobunolol and acetazolamide; levobunolol and dorzolamide; levobunolol and methazolamide; levobunolol and pilocarpine; levobunolol and carbachol; levobunolol and netarsudil; levobunolol and angiopoietin-1; levobunolol and angiopoietin-2; levobunolol and angiopoietin-3; levobunolol and angiopoietin-4; levobunolol and CNTF; levobunolol and Peptide 6; levobunolol and Peptide 21; levobunolol and recombinant CNTF; levobunolol and NGF; levobunolol and BDNF; levobunolol and GDNF; levobunolol and C-type Natriuretic Peptide; levobunolol and natural C-type Natriuretic Peptide; levobunolol and Natriuretic Peptide Receptor-B; levobunolol and bicyclol; levobunolol and FLIP; levobunolol and MET12; levobunolol and compound 1 from Table 1; levobunolol and compound 2 from Table 1; levobunolol and compound 3 from Table 1; levobunolol and compound 4 from Table 1; levobunolol and compound 5 from Table 1; levobunolol and compound 6 from Table 1; levobunolol and compound 7 from Table 1; levobunolol and compound 8 from Table 1; levobunolol and compound 9 from Table 1; levobunolol and compound 10 from Table 1; levobunolol and compound 11 from Table 1; levobunolol and H$^{60}$HIYLGATNYIY$^{71}$-NH$_2$ (SEQ ID NO: 4); levobunolol and FAIM; levobunolol and NOL3; levobunolol and DcR1; levobunolol and DcR2; levobunolol and DcR3; metipranolol and brimonidine; metipranolol and apraclonidine; metipranolol and brinzolamide; metipranolol and acetazolamide; metipranolol and dorzolamide; metipranolol and methazolamide; metipranolol and pilocarpine; metipranolol and carbachol; metipranolol and netarsudil; metipranolol and angiopoietin-1; metipranolol and angiopoietin-2; metipranolol and angiopoietin-3; metipranolol and angiopoietin-4; metipranolol and CNTF; metipranolol and Peptide 6; metipranolol and Peptide 21; metipranolol and recombinant CNTF; metipranolol and NGF; metipranolol and BDNF; metipranolol and GDNF; metipranolol and C-type Natriuretic Peptide; metipranolol and natural C-type Natriuretic Peptide; metipranolol and Natriuretic Peptide Receptor-B; metipranolol and bicyclol; metipranolol and FLIP; metipranolol and MET12; metipranolol and compound 1 from Table 1; metipranolol and compound 2 from Table 1; metipranolol and compound 3 from Table 1; metipranolol and compound 4 from Table 1; metipranolol and compound 5 from Table 1; metipranolol and compound 6 from Table 1; metipranolol and compound 7 from Table 1; metipranolol and compound 8 from Table 1; metipranolol and compound 9 from Table 1; metipranolol and compound 10 from Table 1; metipranolol and compound 11 from Table 1; metipranolol and H$^{60}$HIYLGATNYIY$^{71}$-NH$_2$ (SEQ ID NO: 4); metipranolol and FAIM; metipranolol and NOL3; metipranolol and DcR1; metipranolol and DcR2; metipranolol and DcR3; brimonidine and apraclonidine; brimonidine and brinzolamide; brimonidine and acetazolamide; brimonidine and dorzolamide; brimonidine and methazolamide; brimonidine and pilocarpine; brimonidine and carbachol; brimonidine and netarsudil; brimonidine and angiopoietin-1; brimonidine and angiopoietin-2; brimonidine and angiopoietin-3; brimonidine and angiopoietin-4; brimonidine and CNTF; brimonidine and Peptide 6; brimonidine and Peptide 21; brimonidine and recombinant CNTF; brimonidine and NGF; brimonidine and BDNF; brimonidine and GDNF; brimonidine and C-type Natriuretic Peptide; brimonidine and natural C-type Natriuretic Peptide; brimonidine and Natriuretic Peptide Receptor-B; brimonidine and bicyclol; brimonidine and FLIP; brimonidine and MET12; brimonidine and compound 1 from Table 1; brimonidine and compound 2 from Table 1; brimonidine and compound 3 from Table 1; brimonidine and compound 4 from Table 1; brimonidine and compound 5 from Table 1; brimonidine and compound 6 from Table 1; brimonidine and compound 7 from Table 1; brimonidine and compound 8 from Table 1; brimonidine and compound 9 from Table 1; brimonidine and compound 10 from Table 1; brimonidine and compound 11 from Table 1; brimonidine and H$^{60}$HIYLGATNYIY$^{71}$-NH$_2$ (SEQ ID NO: 4); brimonidine and FAIM; brimonidine and NOL3; brimonidine and DcR1; brimonidine and DcR2; brimonidine and DcR3; apraclonidine and brinzolamide; apraclonidine and acetazolamide; apraclonidine and dorzolamide; apraclonidine and methazolamide; apraclonidine and pilocarpine; apraclonidine and carbachol; apraclonidine and netarsudil; apraclonidine and angiopoietin-1; apraclonidine and angiopoietin-2; apraclonidine and angiopoietin-3; apraclonidine and angiopoietin-4; apraclonidine and CNTF;

apraclonidine and Peptide 6; apraclonidine and Peptide 21; apraclonidine and recombinant CNTF; apraclonidine and NGF; apraclonidine and BDNF; apraclonidine and GDNF; apraclonidine and C-type Natriuretic Peptide; apraclonidine and natural C-type Natriuretic Peptide; apraclonidine and Natriuretic Peptide Receptor-B; apraclonidine and bicyclol; apraclonidine and FLIP; apraclonidine and MET12; apraclonidine and compound 1 from Table 1; apraclonidine and compound 2 from Table 1; apraclonidine and compound 3 from Table 1; apraclonidine and compound 4 from Table 1; apraclonidine and compound 5 from Table 1; apraclonidine and compound 6 from Table 1; apraclonidine and compound 7 from Table 1; apraclonidine and compound 8 from Table 1; apraclonidine and compound 9 from Table 1; apraclonidine and compound 10 from Table 1; apraclonidine and compound 11 from Table 1; apraclonidine and $H^{60}HIYLGATNYIY^{71}$-$NH_2$ (SEQ ID NO: 4); apraclonidine and FAIM; apraclonidine and NOL3; apraclonidine and DcR1; apraclonidine and DcR2; apraclonidine and DcR3; brinzolamide and acetazolamide; brinzolamide and dorzolamide; brinzolamide and methazolamide; brinzolamide and pilocarpine; brinzolamide and carbachol; brinzolamide and netarsudil; brinzolamide and angiopoietin-1; brinzolamide and angiopoietin-2; brinzolamide and angiopoietin-3; brinzolamide and angiopoietin-4; brinzolamide and CNTF; brinzolamide and Peptide 6; brinzolamide and Peptide 21; brinzolamide and recombinant CNTF; brinzolamide and NGF; brinzolamide and BDNF; brinzolamide and GDNF; brinzolamide and C-type Natriuretic Peptide; brinzolamide and natural C-type Natriuretic Peptide; brinzolamide and Natriuretic Peptide Receptor-B; brinzolamide and bicyclol; brinzolamide and FLIP; brinzolamide and MET12; brinzolamide and compound 1 from Table 1; brinzolamide and compound 2 from Table 1; brinzolamide and compound 3 from Table 1; brinzolamide and compound 4 from Table 1; brinzolamide and compound 5 from Table 1; brinzolamide and compound 6 from Table 1; brinzolamide and compound 7 from Table 1; brinzolamide and compound 8 from Table 1; brinzolamide and compound 9 from Table 1; brinzolamide and compound 10 from Table 1; brinzolamide and compound 11 from Table 1; brinzolamide and $H^{60}HIYLGATNYIY^{71}$-$NH_2$ (SEQ ID NO: 4); brinzolamide and FAIM; brinzolamide and NOL3; brinzolamide and DcR1; brinzolamide and DcR2; brinzolamide and DcR3; acetazolamide and dorzolamide; acetazolamide and methazolamide; acetazolamide and pilocarpine; acetazolamide and carbachol; acetazolamide and netarsudil; acetazolamide and angiopoietin-1; acetazolamide and angiopoietin-2; acetazolamide and angiopoietin-3; acetazolamide and angiopoietin-4; acetazolamide and CNTF; acetazolamide and Peptide 6; acetazolamide and Peptide 21; acetazolamide and recombinant CNTF; acetazolamide and NGF; acetazolamide and BDNF; acetazolamide and GDNF; acetazolamide and C-type Natriuretic Peptide; acetazolamide and natural C-type Natriuretic Peptide; acetazolamide and Natriuretic Peptide Receptor-B; acetazolamide and bicyclol; acetazolamide and FLIP; acetazolamide and MET12; acetazolamide and compound 1 from Table 1; acetazolamide and compound 2 from Table 1; acetazolamide and compound 3 from Table 1; acetazolamide and compound 4 from Table 1; acetazolamide and compound 5 from Table 1; acetazolamide and compound 6 from Table 1; acetazolamide and compound 7 from Table 1; acetazolamide and compound 8 from Table 1; acetazolamide and compound 9 from Table 1; acetazolamide and compound 10 from Table 1; acetazolamide and compound 11 from Table 1; acetazolamide and $H^{60}HIYLGATNYIY^{71}$-$NH_2$ (SEQ ID NO: 4); acetazolamide and FAIM; acetazolamide and NOL3; acetazolamide and DcR1; acetazolamide and DcR2; acetazolamide and DcR3; dorzolamide and methazolamide; dorzolamide and pilocarpine; dorzolamide and carbachol; dorzolamide and netarsudil; dorzolamide and angiopoietin-1; dorzolamide and angiopoietin-2; dorzolamide and angiopoietin-3; dorzolamide and angiopoietin-4; dorzolamide and CNTF; dorzolamide and Peptide 6; dorzolamide and Peptide 21; dorzolamide and recombinant CNTF; dorzolamide and NGF; dorzolamide and BDNF; dorzolamide and GDNF; dorzolamide and C-type Natriuretic Peptide; dorzolamide and natural C-type Natriuretic Peptide; dorzolamide and Natriuretic Peptide Receptor-B; dorzolamide and bicyclol; dorzolamide and FLIP; dorzolamide and MET12; dorzolamide and compound 1 from Table 1; dorzolamide and compound 2 from Table 1; dorzolamide and compound 3 from Table 1; dorzolamide and compound 4 from Table 1; dorzolamide and compound 5 from Table 1; dorzolamide and compound 6 from Table 1; dorzolamide and compound 7 from Table 1; dorzolamide and compound 8 from Table 1; dorzolamide and compound 9 from Table 1; dorzolamide and compound 10 from Table 1; dorzolamide and compound 11 from Table 1; dorzolamide and $H^{60}HIYLGATNYIY^{71}$-$NH_2$ (SEQ ID NO: 4); dorzolamide and FAIM; dorzolamide and NOL3; dorzolamide and DcR1; dorzolamide and DcR2; dorzolamide and DcR3; methazolamide and pilocarpine; methazolamide and carbachol; methazolamide and netarsudil; methazolamide and angiopoietin-1; methazolamide and angiopoietin-2; methazolamide and angiopoietin-3; methazolamide and angiopoietin-4; methazolamide and CNTF; methazolamide and Peptide 6; methazolamide and Peptide 21; methazolamide and recombinant CNTF; methazolamide and NGF; methazolamide and BDNF; methazolamide and GDNF; methazolamide and C-type Natriuretic Peptide; methazolamide and natural C-type Natriuretic Peptide; Peptide Receptor-B; methazolamide and Natriuretic Peptide Receptor-B; methazolamide and bicyclol; methazolamide and FLIP; methazolamide and MET12; methazolamide and compound 1 from Table 1; methazolamide and compound 2 from Table 1; methazolamide and compound 3 from Table 1; methazolamide and compound 4 from Table 1; methazolamide and compound 5 from Table 1; methazolamide and compound 6 from Table 1; methazolamide and compound 7 from Table 1; methazolamide and compound 8 from Table 1; methazolamide and compound 9 from Table 1; methazolamide and compound 10 from Table 1; methazolamide and compound 11 from Table 1; methazolamide and $H^{60}HIYLGATNYIY^{71}$-$NH_2$ (SEQ ID NO: 4); methazolamide and FAIM; methazolamide and NOL3; methazolamide and DcR1; methazolamide and DcR2; methazolamide and DcR3; pilocarpine and carbachol; pilocarpine and netarsudil; pilocarpine and angiopoietin-1; pilocarpine and angiopoietin-2; pilocarpine and angiopoietin-3; pilocarpine and angiopoietin-4; pilocarpine and CNTF; pilocarpine and Peptide 6; pilocarpine and Peptide 21; pilocarpine and recombinant CNTF; pilocarpine and NGF; pilocarpine and BDNF; pilocarpine and GDNF; pilocarpine and C-type Natriuretic Peptide; pilocarpine and natural C-type Natriuretic Peptide; pilocarpine and Natriuretic Peptide Receptor-B; pilocarpine and bicyclol; pilocarpine and FLIP; pilocarpine and MET12; pilocarpine and compound 1 from Table 1; pilocarpine and compound 2 from Table 1; pilocarpine and compound 3 from Table 1; pilocarpine and compound 4 from Table 1; pilocarpine and compound 5 from Table 1; pilocarpine and compound 6 from Table 1; pilocarpine and compound 7 from Table 1; pilocarpine and compound 8 from Table 1; pilocarpine and compound 9 from Table 1; pilocarpine and compound 10 from Table 1; pilocarpine and compound 11 from Table 1; pilocarpine and H$^{60}$HIYLGATNYIY$^{71}$-NH$_2$ (SEQ ID NO: 4); pilocarpine and FAIM; pilocarpine and NOL3; pilocarpine and DcR1; pilocarpine and DcR2; pilocarpine and DcR3; carbachol and netarsudil; carbachol and angiopoietin-1; carbachol and angiopoietin-2; carbachol and angiopoietin-3; carbachol and angiopoietin-4; carbachol and CNTF; carbachol and Peptide 6; carbachol and Peptide 21; carbachol and recombinant CNTF; carbachol and NGF; carbachol and BDNF; carbachol and GDNF; carbachol and C-type Natriuretic Peptide; carbachol and natural C-type Natriuretic Peptide; carbachol and Natriuretic Peptide Receptor-B; carbachol and bicyclol; carbachol and FLIP; carbachol and MET12; carbachol and compound 1 from Table 1; carbachol and compound 2 from Table 1; carbachol and compound 3 from Table 1; carbachol and compound 4 from Table 1; carbachol and compound 5 from Table 1; carbachol and compound 6 from Table 1; carbachol and compound 7 from Table 1; carbachol and compound 8 from Table 1; carbachol and compound 9 from Table 1; carbachol and compound 10 from Table 1; carbachol and compound 11 from Table 1; carbachol and H$^{60}$HIYLGATNYIY$^{71}$-NH$_2$ (SEQ ID NO: 4); carbachol and FAIM; carbachol and NOL3; carbachol and DcR1; carbachol and DcR2; carbachol and DcR3; netarsudil and angiopoietin-1; netarsudil and angiopoietin-2; netarsudil and angiopoietin-3; netarsudil and angiopoietin-4; netarsudil and CNTF; netarsudil and Peptide 6; netarsudil and Peptide 21; netarsudil and recombinant CNTF; netarsudil and NGF; netarsudil and BDNF; netarsudil and GDNF; netarsudil and C-type Natriuretic Peptide; netarsudil and natural C-type Natriuretic Peptide; netarsudil and Natriuretic Peptide Receptor-B; netarsudil and bicyclol; netarsudil and FLIP; netarsudil and MET12; netarsudil and compound 1 from Table 1; netarsudil and compound 2 from Table 1; netarsudil and compound 3 from Table 1; netarsudil and compound 4 from Table 1; netarsudil and compound 5 from Table 1; netarsudil and compound 6 from Table 1; netarsudil and compound 7 from Table 1; netarsudil and compound 8 from Table 1; netarsudil and compound 9 from Table 1; netarsudil and compound 10 from Table 1; netarsudil and compound 11 from Table 1; netarsudil and H$^{60}$HIYLGATNYIY$^{71}$-NH$_2$ (SEQ ID NO: 4); netarsudil and FAIM; netarsudil and NOL3; netarsudil and DcR1; netarsudil and DcR2; netarsudil and DcR3; angiopoietin-1 and angiopoietin-2; angiopoietin-1 and angiopoietin-3; angiopoietin-1 and angiopoietin-4; angiopoietin-1 and CNTF; angiopoietin-1 and Peptide 6; angiopoietin-1 and Peptide 21; angiopoietin-1 and recombinant CNTF; angiopoietin-1 and NGF; angiopoietin-1 and BDNF; angiopoietin-1 and GDNF; angiopoietin-1 and C-type Natriuretic Peptide; angiopoietin-1 and natural C-type Natriuretic Peptide; angiopoietin-1 and Natriuretic Peptide Receptor-B; angiopoietin-1 and bicyclol; angiopoietin-1 and FLIP; angiopoietin-1 and MET12; angiopoietin-1 and compound 1 from Table 1; angiopoietin-1 and compound 2 from Table 1; angiopoietin-1 and compound 3 from Table 1; angiopoietin-1 and compound 4 from Table 1; angiopoietin-1 and compound 5 from Table 1; angiopoietin-1 and compound 6 from Table 1; angiopoietin-1 and compound 7 from Table 1; angiopoietin-1 and compound 8 from Table 1; angiopoietin-1 and compound 9 from Table 1; angiopoietin-1 and compound 10 from Table 1; angiopoietin-1 and compound 11 from Table 1; angiopoietin-1 and H$^{60}$HIYLGATNYIY$^{71}$-NH$_2$ (SEQ ID NO: 4); angiopoietin-1 and FAIM; angiopoietin-1 and NOL3; angiopoietin-1 and DcR1; angiopoietin-1 and DcR2; angiopoietin-1 and DcR3; angiopoietin-2 and angiopoietin-3; angiopoietin-2 and angiopoietin-4; angiopoietin-2 and CNTF; angiopoietin-2 and Peptide 6; angiopoietin-2 and Peptide 21; angiopoietin-2 and recombinant CNTF; angiopoietin-2 and NGF; angiopoietin-2 and BDNF; angiopoietin-2 and GDNF; angiopoietin-2 and C-type Natriuretic Peptide; angiopoietin-2 and natural C-type Natriuretic Peptide; angiopoietin-2 and Natriuretic Peptide Receptor-B; angiopoietin-2 and bicyclol; angiopoietin-2 and FLIP; angiopoietin-2 and MET12; angiopoietin-2 and compound 1 from Table 1; angiopoietin-2 and compound 2 from Table 1; angiopoietin-2 and compound 3 from Table 1; angiopoietin-2 and compound 4 from Table 1; angiopoietin-2 and compound 5 from Table 1; angiopoietin-2 and compound 6 from Table 1; angiopoietin-2 and compound 7 from Table 1; angiopoietin-2 and compound 8 from Table 1; angiopoietin-2 and compound 9 from Table 1; angiopoietin-2 and compound 10 from Table 1; angiopoietin-2 and compound 11 from Table 1; angiopoietin-2 and H$^{60}$HIYLGATNYIY$^{71}$-NH$_2$ (SEQ ID NO: 4); angiopoietin-2 and FAIM; angiopoietin-2 and NOL3; angiopoietin-2 and DcR1; angiopoietin-2 and DcR2; angiopoietin-2 and DcR3; angiopoietin-3 and angiopoietin-4; angiopoietin-3 and CNTF; angiopoietin-3 and Peptide 6; angiopoietin-3 and Peptide 21; angiopoietin-3 and recombinant CNTF; angiopoietin-3 and NGF; angiopoietin-3 and BDNF; angiopoietin-3 and GDNF; angiopoietin-3 and C-type Natriuretic Peptide; angiopoietin-3 and natural C-type Natriuretic Peptide; angiopoietin-3 and Natriuretic Peptide Receptor-B; angiopoietin-3 and bicyclol; angiopoietin-3 and FLIP; angiopoietin-3 and MET12; angiopoietin-3 and compound 1 from Table 1; angiopoietin-3 and compound 2 from Table 1; angiopoietin-3 and compound 3 from Table 1; angiopoietin-3 and compound 4 from Table 1; angiopoietin-3 and compound 5 from Table 1; angiopoietin-3 and compound 6 from Table 1; angiopoietin-3 and compound 7 from Table 1; angiopoietin-3 and compound 8 from Table 1; angiopoietin-3 and compound 9 from Table 1; angiopoietin-3 and compound 10 from Table 1; angiopoietin-3 and compound 11 from Table 1; angiopoietin-3 and H$^{60}$HIYLGATNYIY$^{71}$-NH$_2$ (SEQ ID NO: 4); angiopoietin-3 and FAIM; angiopoietin-3 and NOL3; angiopoietin-3 and DcR1; angiopoietin-3 and DcR2; angiopoietin-3 and DcR3; angiopoietin-4 and CNTF; angiopoietin-4 and Peptide 6; angiopoietin-4 and Peptide 21; angiopoietin-4 and recombinant CNTF; angiopoietin-4 and NGF; angiopoietin-4 and BDNF; angiopoietin-4 and GDNF; angiopoietin-4 and C-type Natriuretic Peptide; angiopoietin-4 and natural C-type Natriuretic Peptide; angiopoietin-4 and Natriuretic Peptide Receptor-B; angiopoietin-4 and bicyclol; angiopoietin-4 and FLIP; angiopoietin-4 and MET12; angiopoietin-4 and compound 1 from Table 1; angiopoietin-4 and compound 2 from Table 1; angiopoietin-4 and compound 3 from Table 1; angiopoietin-4 and compound 4 from Table 1; angiopoietin-4 and compound 5 from Table 1; angiopoietin-4 and compound 6 from Table 1; angiopoietin-4 and compound 7 from Table 1; angiopoietin-4 and compound 8 from Table 1; angiopoietin-4 and compound 9 from Table 1; angiopoietin-4 and compound 10 from Table 1; angiopoietin-4 and compound 11 from Table 1; angiopoietin-4 and H$^{60}$HIYLGATNYIY$^{71}$-NH$_2$ (SEQ ID NO: 4); angiopoietin-4 and FAIM; angiopoietin-4 and NOL3; angiopoietin-4 and DcR1; angiopoietin-4 and DcR2; angiopoietin-4 and DcR3; CNTF and Peptide 6; CNTF and Peptide 21; CNTF and recombinant CNTF; CNTF and NGF; CNTF and BDNF; CNTF and GDNF; CNTF and C-type Natriuretic Peptide; CNTF and natural C-type Natriuretic Peptide; CNTF and Natriuretic Peptide Receptor-B; CNTF and bicyclol; CNTF and FLIP; CNTF and MET12; CNTF and compound 1 from Table 1; CNTF and compound 2 from Table 1; CNTF and compound 3 from Table 1; CNTF and compound 4 from Table 1; CNTF and compound 5 from Table 1; CNTF and compound 6 from Table 1; CNTF and compound 7 from Table 1; CNTF and compound 8 from Table 1; CNTF and compound 9 from Table 1; CNTF and compound 10 from Table 1; CNTF and compound 11 from Table 1; CNTF and H$^{60}$HIYLGATNYIY$^{71}$-NH$_2$ (SEQ ID NO: 4); CNTF and FAIM; CNTF and NOL3; CNTF and DcR1; CNTF and DcR2; CNTF and DcR3; Peptide 6 and Peptide 21; Peptide 6 and recombinant Peptide 6; Peptide 6 and NGF; Peptide 6 and BDNF; Peptide 6 and GDNF; Peptide 6 and C-type Natriuretic Peptide; Peptide 6 and natural C-type Natriuretic Peptide; Peptide 6 and Natriuretic Peptide Receptor-B; Peptide 6 and bicyclol; Peptide 6 and FLIP; Peptide 6 and MET12; Peptide 6 and compound 1 from Table 1; Peptide 6 and compound 2 from Table 1; Peptide 6 and compound 3 from Table 1; Peptide 6 and compound 4 from Table 1; Peptide 6 and compound 5 from Table 1; Peptide 6 and compound 6 from Table 1; Peptide 6 and compound 7 from Table 1; Peptide 6 and compound 8 from Table 1; Peptide 6 and compound 9 from Table 1; Peptide 6 and compound 10 from Table 1; Peptide 6 and compound 11 from Table 1; Peptide 6 and H$^{60}$HIYLGATNYIY$^{71}$-NH$_2$ (SEQ ID NO: 4); Peptide 6 and FAIM; Peptide 6 and NOL3; Peptide 6 and DcR1; Peptide 6 and DcR2; Peptide 6 and DcR3; Peptide 21 and recombinant Peptide 21; Peptide 21 and NGF; Peptide 21 and BDNF; Peptide 21 and GDNF; Peptide 21 and C-type Natriuretic Peptide; Peptide 21 and natural C-type Natriuretic Peptide; Peptide 21 and Natriuretic Peptide Receptor-B; Peptide 21 and bicyclol; Peptide 21 and FLIP; Peptide 21 and MET12; Peptide 21 and compound 1 from Table 1; Peptide 21 and compound 2 from Table 1; Peptide 21 and compound 3 from Table 1; Peptide 21 and compound 4 from Table 1; Peptide 21 and compound 5 from Table 1; Peptide 21 and compound 6 from Table 1; Peptide 21 and compound 7 from Table 1; Peptide 21 and compound 8 from Table 1; Peptide 21 and compound 9 from Table 1; Peptide 21 and compound 10 from Table 1; Peptide 21 and compound 11 from Table 1; Peptide 21 and H$^{60}$HIYLGATNYIY$^{71}$-NH$_2$ (SEQ ID NO: 4); Peptide 21 and FAIM; Peptide 21 and NOL3; Peptide 21 and DcR1; Peptide 21 and DcR2; Peptide 21 and DcR3; recombinant Peptide 21 and NGF; recombinant Peptide 21 and BDNF; recombinant Peptide 21 and GDNF; recombinant Peptide 21 and C-type Natriuretic Peptide; recombinant Peptide 21 and natural C-type Natriuretic Peptide; recombinant Peptide 21 and Natriuretic Peptide Receptor-B; recombinant Peptide 21 and bicyclol; recombinant Peptide 21 and FLIP; recombinant Peptide 21 and MET12; recombinant Peptide 21 and compound 1 from Table 1; recombinant Peptide 21 and compound 2 from Table 1; recombinant Peptide 21 and compound 3 from Table 1; recombinant Peptide 21 and compound 4 from Table 1; recombinant Peptide 21 and compound 5 from Table 1; recombinant Peptide 21 and compound 6 from Table 1; recombinant Peptide 21 and compound 7 from Table 1; recombinant Peptide 21 and compound 8 from Table 1; recombinant Peptide 21 and compound 9 from Table 1; recombinant Peptide 21 and compound 10 from Table 1; recombinant Peptide 21 and compound 11 from Table 1; recombinant Peptide 21 and H$^{60}$HIYLGATNYIY$^{71}$-NH$_2$ (SEQ ID NO: 4); recombinant Peptide 21 and FAIM; recombinant Peptide 21 and NOL3; recombinant Peptide 21 and DcR1; recombinant Peptide 21 and DcR2; recombinant Peptide 21 and DcR3; NGF and BDNF; NGF and GDNF; NGF and C-type Natriuretic Peptide; NGF and natural C-type Natriuretic Peptide; NGF and Natriuretic Peptide Receptor-B; NGF and bicyclol; NGF and FLIP; NGF and MET12; NGF and compound 1 from Table 1; NGF and compound 2 from Table 1; NGF and compound 3 from Table 1; NGF and compound 4 from Table 1; NGF and compound 5 from Table 1; NGF and compound 6 from Table 1; NGF and compound 7 from Table 1; NGF and compound 8 from Table 1; NGF and compound 9 from Table 1; NGF and compound 10 from Table 1; NGF and compound 11 from Table 1; NGF and H$^{60}$HIYLGATNYIY$^{71}$-NH$_2$ (SEQ ID NO: 4); NGF and FAIM; NGF and NOL3; NGF and DcR1; NGF and DcR2; NGF and DcR3; BDNF and GDNF; BDNF and C-type Natriuretic Peptide; BDNF and natural C-type Natriuretic Peptide; BDNF and Natriuretic Peptide Receptor-B; BDNF and bicyclol; BDNF and FLIP; BDNF and MET12; BDNF and compound 1 from Table 1; BDNF and compound 2 from Table 1; BDNF and compound 3 from Table 1; BDNF and compound 4 from Table 1; BDNF and compound 5 from Table 1; BDNF and compound 6 from Table 1; BDNF and compound 7 from Table 1; BDNF and compound 8 from Table 1; BDNF and compound 9 from Table 1; BDNF and compound 10 from Table 1; BDNF and compound 11 from Table 1; BDNF and H$^{60}$HIYLGATNYIY$^{71}$-NH$_2$ (SEQ ID NO: 4); BDNF and FAIM; BDNF and NOL3; BDNF and DcR1; BDNF and DcR2; BDNF and DcR3; GDNF and C-type Natriuretic Peptide; GDNF and natural C-type Natriuretic Peptide; GDNF and Natriuretic Peptide Receptor-B; GDNF and bicyclol; GDNF and FLIP; GDNF and MET12; GDNF and compound 1 from Table 1; GDNF and compound 2 from Table 1; GDNF and compound 3 from Table 1; GDNF and compound 4 from Table 1; GDNF and compound 5 from Table 1; GDNF and compound 6 from Table 1; GDNF and compound 7 from Table 1; GDNF and compound 8 from Table 1; GDNF and compound 9 from Table 1; GDNF and compound 10 from Table 1; GDNF and compound 11 from Table 1; GDNF and H$^{60}$HIYLGATNYIY$^{71}$-NH$_2$ (SEQ ID NO: 4); GDNF and FAIM; GDNF and NOL3; GDNF and DcR1; GDNF and DcR2; GDNF and DcR3; C-type Natriuretic Peptide and natural C-type Natriuretic Peptide; C-type Natriuretic Peptide and Natriuretic Peptide Receptor-B; C-type Natriuretic Peptide and bicyclol; C-type Natriuretic Peptide and FLIP; C-type Natriuretic Peptide and MET12; C-type Natriuretic Peptide and compound 1 from Table 1; C-type Natriuretic Peptide and compound 2 from Table 1; C-type Natriuretic Peptide and compound 3 from Table 1; C-type Natriuretic Peptide and compound 4 from Table 1; C-type Natriuretic Peptide and compound 5 from Table 1; C-type Natriuretic Peptide and compound 6 from Table 1; C-type Natriuretic Peptide and compound 7 from Table 1; C-type Natriuretic Peptide and compound 8 from Table 1; C-type Natriuretic Peptide and compound 9 from Table 1; C-type Natriuretic Peptide and compound 10 from Table 1; C-type Natriuretic Peptide and compound 11 from Table 1; C-type Natriuretic Peptide and H$^{60}$HIYLGATNYIY$^{71}$-NH$_2$ (SEQ ID NO: 4); C-type Natriuretic Peptide and FAIM; C-type Natriuretic Peptide and NOL3; C-type Natriuretic Peptide and DcR1; C-type Natriuretic Peptide and DcR2; C-type Natriuretic Peptide and DcR3; natural C-type Natriuretic Peptide and Natriuretic Peptide Receptor-B; natural C-type Natriuretic Peptide and bicyclol; natural C-type Natriuretic Peptide and FLIP; natural C-type Natriuretic Peptide and MET12; natural C-type Natriuretic Peptide and compound 1 from Table 1; natural C-type Natriuretic Peptide and compound 2 from Table 1; natural C-type Natriuretic Peptide and compound 3 from Table 1; natural C-type Natriuretic Peptide and compound 4 from Table 1; natural C-type Natriuretic Peptide and compound 5 from Table 1; natural C-type Natriuretic Peptide and compound 6 from Table 1; natural C-type Natriuretic Peptide and compound 7 from Table 1; natural C-type Natriuretic Peptide and compound 8 from Table 1; natural C-type Natriuretic Peptide and compound 9 from Table 1; natural C-type Natriuretic Peptide and compound 10 from Table 1; natural C-type Natriuretic Peptide and compound 11 from Table 1; natural C-type Natriuretic Peptide and $H^{60}HIYLGATNYIY^{71}$-$NH_2$ (SEQ ID NO: 4); natural C-type Natriuretic Peptide and FAIM; natural C-type Natriuretic Peptide and NOL3; natural C-type Natriuretic Peptide and DcR1; natural C-type Natriuretic Peptide and DcR2; natural C-type Natriuretic Peptide and DcR3; Natriuretic Peptide Receptor-B and bicyclol; Natriuretic Peptide Receptor-B and FLIP; Natriuretic Peptide Receptor-B and MET12; Natriuretic Peptide Receptor-B and compound 1 from Table 1; Natriuretic Peptide Receptor-B and compound 2 from Table 1; Natriuretic Peptide Receptor-B and compound 3 from Table 1; Natriuretic Peptide Receptor-B and compound 4 from Table 1; Natriuretic Peptide Receptor-B and compound 5 from Table 1; Natriuretic Peptide Receptor-B and compound 6 from Table 1; Natriuretic Peptide Receptor-B and compound 7 from Table 1; Natriuretic Peptide Receptor-B and compound 8 from Table 1; Natriuretic Peptide Receptor-B and compound 9 from Table 1; Natriuretic Peptide Receptor-B and compound 10 from Table 1; Natriuretic Peptide Receptor-B and compound 11 from Table 1; Natriuretic Peptide Receptor-B and $H^{60}HIYLGATNYIY^{71}$-$NH_2$ (SEQ ID NO: 4); Natriuretic Peptide Receptor-B and FAIM; Natriuretic Peptide Receptor-B and NOL3; Natriuretic Peptide Receptor-B and DcR1; Natriuretic Peptide Receptor-B and DcR2; Natriuretic Peptide Receptor-B and DcR3; bicyclol and FLIP; bicyclol and MET12; bicyclol and compound 1 from Table 1; bicyclol and compound 2 from Table 1; bicyclol and compound 3 from Table 1; bicyclol and compound 4 from Table 1; bicyclol and compound 5 from Table 1; bicyclol and compound 6 from Table 1; bicyclol and compound 7 from Table 1; bicyclol and compound 8 from Table 1; bicyclol and compound 9 from Table 1; bicyclol and compound 10 from Table 1; bicyclol and compound 11 from Table 1; bicyclol and $H^{60}HIYLGATNYIY^{71}$-$NH_2$ (SEQ ID NO: 4); bicyclol and FAIM; bicyclol and NOL3; bicyclol and DcR1; bicyclol and DcR2; bicyclol and DcR3; FLIP and MET12; FLIP and compound 1 from Table 1; FLIP and compound 2 from Table 1; FLIP and compound 3 from Table 1; FLIP and compound 4 from Table 1; FLIP and compound 5 from Table 1; FLIP and compound 6 from Table 1; FLIP and compound 7 from Table 1; FLIP and compound 8 from Table 1; FLIP and compound 9 from Table 1; FLIP and compound 10 from Table 1; FLIP and compound 11 from Table 1; FLIP and $H^{60}HIYLGATNYIY^{71}$-$NH_2$ (SEQ ID NO: 4); FLIP and FAIM; FLIP and NOL3; FLIP and DcR1; FLIP and DcR2; FLIP and DcR3; MET12 and compound 1 from Table 1; MET12 and compound 2 from Table 1; MET12 and compound 3 from Table 1; MET12 and compound 4 from Table 1; MET12 and compound 5 from Table 1; MET12 and compound 6 from Table 1; MET12 and compound 7 from Table 1; MET12 and compound 8 from Table 1; MET12 and compound 9 from Table 1; MET12 and compound 10 from Table 1; MET12 and compound 11 from Table 1; MET12 and $H^{60}HIYLGATNYIY^{71}$-$NH_2$ (SEQ ID NO: 4); MET12 and FAIM; MET12 and NOL3; MET12 and DcR1; MET12 and DcR2; MET12 and DcR3; compound 1 from Table 1 and compound 2 from Table 1; compound 1 from Table 1 and compound 3 from Table 1; compound 1 from Table 1 and compound 4 from Table 1; compound 1 from Table 1 and compound 5 from Table 1; compound 1 from Table 1 and compound 6 from Table 1; compound 1 from Table 1 and compound 7 from Table 1; compound 1 from Table 1 and compound 8 from Table 1; compound 1 from Table 1 and compound 9 from Table 1; compound 1 from Table 1 and compound 10 from Table 1; compound 1 from Table 1 and compound 11 from Table 1; compound 1 from Table 1 and $H^{60}HIYLGATNYIY^{71}$-$NH_2$ (SEQ ID NO: 4); compound 1 from Table 1 and FAIM; compound 1 from Table 1 and NOL3; compound 1 from Table 1 and DcR1; compound 1 from Table 1 and DcR2; compound 1 from Table 1 and DcR3; compound 2 from Table 1 and compound 3 from Table 1; compound 2 from Table 1 and compound 4 from Table 1; compound 2 from Table 1 and compound 5 from Table 1; compound 2 from Table 1 and compound 6 from Table 1; compound 2 from Table 1 and compound 7 from Table 1; compound 2 from Table 1 and compound 8 from Table 1; compound 2 from Table 1 and compound 9 from Table 1; compound 2 from Table 1 and compound 10 from Table 1; compound 2 from Table 1 and compound 11 from Table 1; compound 2 from Table 1 and $H^{60}HIYLGATNYIY^{71}$-$NH_2$ (SEQ ID NO: 4); compound 2 from Table 1 and FAIM; compound 2 from Table 1 and NOL3; compound 2 from Table 1 and DcR1; compound 2 from Table 1 and DcR2; compound 2 from Table 1 and DcR3; compound 3 from Table 1 and compound 4 from Table 1; compound 3 from Table 1 and compound 5 from Table 1; compound 3 from Table 1 and compound 6 from Table 1; compound 3 from Table 1 and compound 7 from Table 1; compound 3 from Table 1 and compound 8 from Table 1; compound 3 from Table 1 and compound 9 from Table 1; compound 3 from Table 1 and compound 10 from Table 1; compound 3 from Table 1 and compound 11 from Table 1; compound 3 from Table 1 and $H^{60}HIYLGATNYIY^{71}$-$NH_2$ (SEQ ID NO: 4); compound 3 from Table 1 and FAIM; compound 3 from Table 1 and NOL3; compound 3 from Table 1 and DcR1; compound 3 from Table 1 and DcR2; compound 3 from Table 1 and DcR3; compound 4 from Table 1 and compound 5 from Table 1; compound 4 from Table 1 and compound 6 from Table 1; compound 4 from Table 1 and compound 7 from Table 1; compound 4 from Table 1 and compound 8 from Table 1; compound 4 from Table 1 and compound 9 from Table 1; compound 4 from Table 1 and compound 10 from Table 1; compound 4 from Table 1 and compound 11 from Table 1; compound 4 from Table 1 and $H^{60}HIYLGATNYIY^{71}$-$NH_2$ (SEQ ID NO: 4); compound 4 from Table 1 and FAIM; compound 4 from Table 1 and NOL3; compound 4 from Table 1 and DcR1; compound 4 from Table 1 and DcR2; compound 4 from Table 1 and DcR3; compound 5 from Table 1 and compound 6 from Table 1; compound 5 from Table 1 and compound 7 from Table 1; compound 5 from Table 1 and compound 8 from Table 1; compound 5 from Table 1 and compound 9 from Table 1; compound 5 from Table 1 and compound 10 from Table 1; compound 5 from Table 1 and compound 11 from Table 1; compound 5 from Table 1 and $H^{60}HIYLGATNYIY^{71}$-$NH_2$ (SEQ ID NO: 4); compound 5 from Table 1 and FAIM; compound 5 from Table 1 and NOL3; compound 5 from Table 1 and DcR1; compound 5 from Table 1 and DcR2; compound 5 from Table 1 and DcR3; compound 6 from Table 1 and compound 7 from Table 1; compound 6 from Table 1 and compound 8 from Table 1; compound 6 from Table 1 and compound 9 from Table 1; compound 6 from Table 1 and compound 10 from Table 1; compound 6 from Table 1 and compound 11 from Table 1; compound 6 from Table 1 and H⁶⁰HIYLGATNYIY⁷¹-NH₂ (SEQ ID NO: 4); compound 6 from Table 1 and FAIM; compound 6 from Table 1 and NOL3; compound 6 from Table 1 and DcR1; compound 6 from Table 1 and DcR2; compound 6 from Table 1 and DcR3; compound 7 from Table 1 and compound 8 from Table 1; compound 7 from Table 1 and compound 9 from Table 1; compound 7 from Table 1 and compound 10 from Table 1; compound 7 from Table 1 and compound 11 from Table 1; compound 7 from Table 1 and H⁶⁰HIYLGATNYIY⁷¹-NH₂ (SEQ ID NO: 4); compound 7 from Table 1 and FAIM; compound 7 from Table 1 and NOL3; compound 7 from Table 1 and DcR1; compound 7 from Table 1 and DcR2; compound 7 from Table 1 and DcR3; compound 8 from Table 1 and compound 9 from Table 1; compound 8 from Table 1 and compound 10 from Table 1; compound 8 from Table 1 and compound 11 from Table 1; compound 8 from Table 1 and H⁶⁰HIYLGATNYIY⁷¹-NH₂ (SEQ ID NO: 4); compound 8 from Table 1 and FAIM; compound 8 from Table 1 and NOL3; compound 8 from Table 1 and DcR1; compound 8 from Table 1 and DcR2; compound 8 from Table 1 and DcR3; compound 9 from Table 1 and compound 10 from Table 1; compound 9 from Table 1 and compound 11 from Table 1; compound 9 from Table 1 and H⁶⁰HIYLGATNYIY⁷¹-NH₂ (SEQ ID NO: 4); compound 9 from Table 1 and FAIM; compound 9 from Table 1 and NOL3; compound 9 from Table 1 and DcR1; compound 9 from Table 1 and DcR2; compound 9 from Table 1 and DcR3; compound 10 from Table 1 and compound 11 from Table 1; compound 10 from Table 1 and H⁶⁰HIYLGATNYIY⁷¹-NH₂ (SEQ ID NO: 4); compound 10 from Table 1 and FAIM; compound 10 from Table 1 and NOL3; compound 10 from Table 1 and DcR1; compound 10 from Table 1 and DcR2; compound 10 from Table 1 and DcR3; compound 11 from Table 1 and H⁶⁰HIYLGATNYIY⁷¹-NH₂ (SEQ ID NO: 4); compound 11 from Table 1 and FAIM; compound 11 from Table 1 and NOL3; compound 11 from Table 1 and DcR1; compound 11 from Table 1 and DcR2; compound 11 from Table 1 and DcR3; H⁶⁰HIYLGATNYIY⁷¹-NH₂ (SEQ ID NO: 4) and FAIM; H⁶⁰HIYLGATNYIY⁷¹-NH₂ (SEQ ID NO: 4) and NOL3; H⁶⁰HIYLGATNYIY⁷¹-NH₂ (SEQ ID NO: 4) and DcR1; H⁶⁰HIYLGATNYIY⁷¹-NH₂ (SEQ ID NO: 4) and DcR2; H⁶⁰HIYLGATNYIY⁷¹-NH₂ (SEQ ID NO: 4) and DcR3; FAIM and NOL3; FAIM and DcR1; FAIM and DcR2; FAIM and DcR3; NOL3 and DcR1; NOL3 and DcR2; NOL3 and DcR3; and DcR1 and DcR2; DcR1 and DcR3; DcR2 and DcR3.

Some covalently linked combinations are represented by the following structural formulas:

| | |
|---|---|
| P6-MET12 | Formula C-1. |
| P6-MET12-P6 | Formula C-2. |
| MET12-P6-MET12 | Formula C-3. |
| P6-GGG-MET12 | Formula C-4. |
| MET12-GGG-P6 | Formula C-5. |
| P6-GGG-MET12-GGG-P6 | Formula C-6. |
| MET12-GGG-P6-GGG-MET12 | Formula C-7. |
| P6-(N-AEAc)$_x$-MET12 | Formula C-8. |
| MET12-(N-AEAc)$_x$-P6 | Formula C-9. |
| MET12-(N-AEEAc)$_x$-P6-(N-AEEAc)$_y$-MET12 | Formula C-10. |
| P6-(N-AEEAc)$_x$-MET12-(N-AEEAc)$_y$-P6 | Formula C-11. |
| P6-(N-dPEG12)$_x$-MET12 | Formula C-12. |
| P21-MET12 | Formula C-13. |
| P12-MET12-P21 | Formula C-14. |
| MET12-P21-MET12 | Formula C-15. |
| P21-GGG-MET12 | Formula C-16. |
| MET12-GGG-P21 | Formula C-17. |
| P21-GGG-MET12-GGG-P21 | Formula C-18. |
| MET12-GGG-P21-GGG-MET12 | Formula C-19. |
| P21-(N-AEAc)$_x$-MET12 | Formula C-20. |
| MET12-(N-AEEAc)$_x$-P21 | Formula C-21. |
| MET12-(N-AEEAc)$_x$-P12-(N-AEEAc)$_y$-MET12 | Formula C-22. |
| P21-(N-AEEAc)$_x$-MET12-(N-AEEAc)$_y$-P21 | Formula C-23. |
| P21-(N-dPEG12)$_x$-MET12 | Formula C-24. |
| P6-(O-AEAc)$_x$-MET12 | Formula C-25. |
| MET12-(O-AEEAc)$_x$-P6 | Formula C-26. |
| MET12-(O-AEEAc)$_x$-P6-(O-AEEAc)$_y$-MET12 | Formula C-27. |
| P6-(O-AEEAc)$_x$-MET12-(O-AEEAc)$_y$-P6 | Formula C-28. |
| P6-(O-dPEG12)$_x$-MET12 | Formula C-29. |
| P21-(O-AEAc)$_x$-MET12 | Formula C-30. |
| MET12-(O-AEEAc)$_x$-P21 | Formula C-31. |
| MET12-(O-AEEAc)$_x$-P21-(O-AEEAc)$_y$-MET12 | Formula C-32. |
| P21-(O-AEEAc)$_x$-MET12-(O-AEEAc)$_y$-P21 | Formula C-33. |
| P21-(O-dPEG12)$_x$-MET | Formula C-34. |
| P6-MET12-BC | Formula C-35. |
| P6-MET12-P6-BC | Formula C-36. |
| MET12-P6-MET12-BC | Formula C-37. |
| P6-GGG-MET12-BC | Formula C-38. |
| MET12-GGG-P6-BC | Formula C-39. |
| P6-GGG-MET12-GGG-P6-BC | Formula C-40. |
| MET12-GGG-P6-GGG-MET12-BC | Formula C-41. |
| P6-(N-AEAc)$_x$-MET12-BC | Formula C-42. |
| MET12-(N-AEEAc)$_x$-P6-BC | Formula C-43. |
| MET12-(N-AEEAc)$_x$-P6-(N-AEEAc)$_y$-MET12-BC | Formula C-44. |
| P6-(N-AEEAc)$_x$-MET12-(N-AEEAc)$_y$-P6-BC | Formula C-45. |
| P6-(N-dPEG12)$_x$-MET12-BC | Formula C-46. |

| | | | |
|---|---|---|---|
| P21-MET12-BC | Formula C-47. | BC-P21-GGG-MET12 | Formula C-84. |
| P21-MET12-P21-BC | Formula C-48. | BC-MET12-GGG-P21 | Formula C-85. |
| MET12-P21-MET12-BC | Formula C-49. | BC-P21-GGG-MET12-GGG-P21 | Formula C-86. |
| P21-GGG-MET12-BC | Formula C-50. | BC-MET12-GGG-P21-GGG-MET12 | Formula C-87. |
| MET12-GGG-P21-BC | Formula C-51. | BC-P21-(N-AEAc)$_x$-MET12 | Formula C-88. |
| P21-GGG-MET12-GGG-P21-BC | Formula C-52. | BC-MET12-(N-AEEAc)$_x$-P21 | Formula C-89. |
| MET12-GGG-P21-GGG-MET12-BC | Formula C-53. | BC-MET12-(N-AEEAc)$_x$-P21-(N-AEEAc)$_y$-MET12 | Formula C-90. |
| P21-(N-AEAc)$_x$-MET12-BC | Formula C-54. | BC-P21-(N-AEEAc)$_x$-MET12-(N-AEEAc)$_y$-P21 | Formula C-91. |
| MET12-(N-AEEAc)$_x$-P21-BC | Formula C-55. | BC-P21-(N-dPEG12)$_x$-MET12 | Formula C-92. |
| MET12-(N-AEEAc)$_x$-P21-(N-AEEAc)$_y$-MET12-BC | Formula C-56. | BC-P6-(O-AEAc)$_x$-MET12 | Formula C-93. |
| P21-(N-AEEAc)$_x$-MET12-(N-AEEAc)$_y$-P21-BC | Formula C-57. | BC-MET12-(O-AEEAc)$_x$-P6 | Formula C-94. |
| P21-(N-dPEG12)$_x$-MET12-BC | Formula C-58. | BC-MET12-(O-AEEAc)$_x$-P6-(O-AEEAc)$_y$-MET12 | Formula C-95. |
| P6-(O-AEAc)$_x$-MET12-BC | Formula C-59. | BC-P6-(O-AEEAc)$_x$-MET12-(O-AEEAc)$_y$-P6 | Formula C-96. |
| MET12-(O-AEEAc)$_x$-P6-BC | Formula C-60. | BC-P6-(O-dPEG12)$_x$-MET12 | Formula C-97. |
| MET12-(O-AEEAc)$_x$-P6-(O-AEEAc)$_y$-MET12-BC | Formula C-61. | BC-P21-(O-AEAc)$_x$-MET12 | Formula C-98. |
| P6-(O-AEEAc)$_x$-MET12-(O-AEEAc)$_y$-P6-BC | Formula C-62. | BC-MET12-(O-AEEAc)$_x$-P21 | Formula C-99. |
| P6-(O-dPEG12)$_x$-MET12-BC | Formula C-63. | BC-MET12-(O-AEEAc)$_x$-P21-(O-AEEAc)$_y$-MET12 | Formula C-100. |
| P21-(O-AEAc)$_x$-MET12-BC | Formula C-64. | BC-P21-(O-AEEAc)$_x$-MET12-(O-AEEAc)$_y$-P21 | Formula C-101. |
| MET12-(O-AEEAc)$_x$-P21-BC | Formula C-65. | BC-P21-(O-dPEG12)$_x$-MET12 | Formula C-102. |
| MET12-(O-AEEAc)$_x$-P21-(O-AEEAc)$_y$-MET12-BC | Formula C-66. | P6-MET4-8 | Formula C-105. |
| P21-(O-AEEAc)$_x$-MET12-(O-AEEAc)$_y$-P21-BC | Formula C-67. | P6-MET4-8-P6 | Formula C-106. |
| P21-(O-dPEG12)$_x$-MET12-BC | Formula C-68. | MET4-8-P6-MET4-8 | Formula C-107. |
| BC-P6-MET12 | Formula C-69. | P6-GGG-MET4-8 | Formula C-108. |
| BC-P6-MET12-P6 | Formula C-70. | MET4-8-GGG-P6 | Formula C-109. |
| BC-MET12-P6-MET12 | Formula C-71. | P6-GGG-MET4-8-GGG-P6 | Formula C-110. |
| BC-P6-GGG-MET12 | Formula C-72. | MET4-8-GGG-P6-GGG-MET4-8 | Formula C-111. |
| BC-MET12-GGG-P6 | Formula C-73. | P6-(N-AEAc)$_x$-MET4-8 | Formula C-112. |
| BC-P6-GGG-MET12-GGG-P6 | Formula C-74. | MET4-8-(N-AEEAc)$_x$-P6 | Formula C-113. |
| BC-MET12-GGG-P6-GGG-MET12 | Formula C-75. | MET4-8-(N-AEEAc)$_x$-P6-(N-AEEAc)$_y$-MET4-8 | Formula C-114. |
| BC-P6-(N-AEAc)$_x$-MET12 | Formula C-76. | P6-(N-AEEAc)$_x$-MET4-8-(N-AEEAc)$_y$-P6 | Formula C-115. |
| BC-MET12-(N-AEEAc)$_x$-P6 | Formula C-77. | P6-(N-dPEG12)$_x$-MET4-8 | Formula C-116. |
| BC-MET12-(N-AEEAc)$_x$-P6-(N-AEEAc)$_y$-MET12 | Formula C-78. | P21-MET4-8 | Formula C-117. |
| BC-P6-(N-AEEAc)$_x$)-MET12-(N-AEEAc)$_y$-P6 | Formula C-79. | P21-MET4-8-P21 | Formula C-118. |
| BC-P6-(N-dPEG12)$_x$-MET12 | Formula C-80. | MET4-8-P21-MET4-8 | Formula C-119. |
| BC-P21-MET12 | Formula C-81. | P21-GGG-MET4-8 | Formula C-120. |
| BC-P21-MET12-P21 | Formula C-82. | MET4-8-GGG-P21 | Formula C-121. |
| BC-MET12-P21-MET12 | Formula C-83. | P21-GGG-MET4-8-GGG-P21 | Formula C-122. |

| | |
|---|---|
| MET4-8-GGG-P21-GGG-MET4-8 | Formula C-123. |
| P21-(N-AEAc)$_x$-MET4-8 | Formula C-124. |
| MET4-8-(N-AEEAc)$_x$-P21 | Formula C-125. |
| MET4-8-(N-AEEAc)$_x$-P21-(N-AEEAc)$_y$-MET4-8 | Formula C-126. |
| P21-(N-AEEAc)$_x$-MET4-8(N-AEEAc)$_y$-P21 | Formula C-127. |
| P21-(N-dPEG12)$_x$-MET4-8 | Formula C-128. |
| P6-(O-AEAc)$_x$-MET4-8 | C-129. |
| MET4-8-(O-AEEAc)$_x$-P6 | Formula C-130. |
| MET4-8-(O-AEEAc)$_x$-P6-(O-AEEAc)$_y$-MET4-8 | Formula C-131. |
| P6-(O-AEEAc)$_x$-MET4-8-(O-AEEAc)$_y$-P6 | Formula C-132. |
| P6-(O-dPEG12)$_x$-MET4-8 | Formula C-133. |
| P21-(O-AEAc)$_x$-MET4-8 | Formula C-134. |
| MET4-8-(O-AEEAc)$_x$-P21 | Formula C-135. |
| MET4-8-(O-AEEAc)$_x$-P21-(O-AEEAc)$_y$-MET4-8 | Formula C-136. |
| P21-(O-AEEAc)$_x$-MET4-8-(O-AEEAc)$_y$-P21 | Formula C-137. |
| P21-(O-dPEG12)$_x$-MET4-8 | Formula C-138. |
| P6-MET4-8-BC | Formula C-139. |
| P6-MET4-8-P6-BC | Formula C-140. |
| MET4-8-P6-MET4-8-BC | Formula C-141. |
| P6-GGG-MET4-8-BC | Formula C-142. |
| MET4-8-GGG-P6-BC | Formula C-143. |
| P6-GGG-MET4-8-GGG-P6-BC | Formula C-144. |
| MET4-8-GGG-P6-GGG-MET4-8-BC | Formula C-145. |
| P6-(N-AEAc)$_x$-MET4-8-BC | Formula C-146. |
| MET4-8-(N-AEEAc)$_x$-P6-BC | Formula C-147. |
| MET4-8-(N-AEEAc)$_x$-P6-(N-AEEAc)$_y$-MET4-8-BC | Formula C-148. |
| P6-(N-AEEAc)$_x$-MET4-8-(N-AEEAc)$_y$-P6-BC | Equation C-149. |
| P6-(N-dPEG12)$_x$-MET4-8-BC | Formula C-150. |
| P21-MET4-8-BC | Formula C-151. |
| P21-MET4-8-P21-BC | Formula C-152. |
| MET4-8-P21-MET4-8-BC | Formula C-153. |
| P21-GGG-MET4-8-BC | Formula C-154. |
| MET4-8-GGG-P21-BC | Formula C-155. |
| P21-GGG-MET4-8-GGG-P21-BC | Formula C-156. |
| MET4-8-GGG-P21-GGG-MET4-8-BC | Formula C-157. |
| P21-(N-AEAc)$_x$-MET4-8-BC | Formula C-158. |
| MET4-8-(N-AEEAc)$_x$-P21-BC | Formula C-159. |
| MET4-8-(N-AEEAc)$_x$-P21-(N-AEEAc)$_y$-MET4-8-BC | Formula C-160. |
| P21-(N-AEEAc)$_x$-MET4-8-(N-AEEAc)$_y$-P21-BC | Formula C-161. |
| P21-(N-dPEG12)$_x$-MET4-8-BC | Formula C-162. |
| P6-(O-AEAc)$_x$-MET4-8-BC | Formula C-163. |
| MET4-8-(O-AEEAc)$_x$-P6-BC | Formula C-164. |
| MET4-8-(O-AEEAc)$_x$-PG-(O-AEEAc)$_y$-MET4-8-BC | Formula C-165. |
| P6-(O-AEEAc)$_x$-MET4-8-(O-AEEAc)$_y$-P6-BC | Formula C-166. |
| P6-(O-dPEG12)$_x$-MET4-8-BC | Formula C-167. |
| P21-(O-AEAc)$_x$-MET3-8-BC | Formula C-168. |
| MET4-8-(O-AEEAc)$_x$-P21-BC | Formula C-169. |
| MET4-8-(O-AEEAc)$_x$-P21-(O-AEEAc)$_y$-MET4-8-BC | Formula C-170. |
| P21-(O-AEEAc)$_x$-MET4-8-(O-AEEAc)$_y$-P21-BC | Formula C-171. |
| P21-(O-dPEG12)$_x$-MET4-8-BC | Formula C-172. |
| BC-P6-MET4-8 | Formula C-173. |
| BC-P6-MET4-8-P6 | Formula C-174. |
| BC-MET4-8-P6-MET4-8 | Formula C-175. |
| BC-P6-GGG-MET3-4-8 | Formula C-176. |
| BC-MET4-8-GGG-P6 | Formula C-177. |
| BC-P6-GGG-MET4-8-GGG-P6 | Formula C-178. |
| BC-MET4-8-GGG-P6-GGG-MET4-8 | Formula C-179. |
| BC-P6-(N-AEAc)$_x$-MET4-8 | Formula C-180. |
| BC-MET4-8-(N-AEEAc)$_x$-P6 | Formula C-181. |
| BC-MET4-8-(N-AEEAc)$_x$-P6-(N-AEEAc)$_y$-MET4-8 | Formula C-182. |
| BC-P6-(N-AEEAc)$_x$-MET4-8-(N-AEEAc)$_y$-P6 | Formula C-183. |
| BC-P6-(N-dPEG12)$_x$-MET4-8 | Formula C-184. |
| BC-P21-MET4-8 | Formula C-185. |
| BC-P21-MET4-8-P21 | Formula C-186. |
| BC-MET4-8-P21-MET4-8 | Formula C-187. |
| BC-P21-GGG-MET4-8 | Formula C-188. |
| BC-MET4-8-GGG-P21 | Formula C-189. |
| BC-P21-GGG-MET4-8-GGG-P21 | Formula C-190. |
| BC-MET4-8-GGG-P21-GGG-MET4-8 | Formula C-191. |
| BC-P21-(N-AEAc)$_x$-MET4-8 | Formula C-192. |
| BC-MET4-8-(N-AEEAc)$_x$-P21 | Formula C-193. |

| | |
|---|---|
| BC-MET4-8-(N-AEEAc)$_x$-P21-(N-AEEAc)$_y$-MET4-8 | Formula C-194. |
| BC-P21-(N-AEEAc)$_x$-MET4-8-(N-AEEAc)$_y$-P21 | Formula C-195. |
| BC-P21-(N-dPEG12)$_x$-MET4-8 | Formula C-196. |
| BC-P6-(O-AEAc)$_x$-MET4-8 | Formula C-197. |
| BC-MET4-8-(O-AEEAc)$_x$-P6 | Formula C-198. |
| BC-MET4-8-(O-AEEAc)$_x$-P6-(O-AEEAc)$_y$-MET4-8 | Formula C-199. |
| BC-P6-(O-AEEAc)$_x$-MET4-8-(O-AEEAc)$_y$-P6 | Formula C-200. |
| BC-P6-(O-dPEG12)$_x$-MET4-8 | Formula C-201. |
| BC-P21-(O-AEAc)$_x$-MET4-8 | Formula C-202. |
| BC-MET4-8-(O-AEEAc)$_x$-P21 | Formula C-203. |
| BC-MET4-8-(O-AEEAc)$_x$-P21-(O-AEEAc)$_y$-MET4-8 | Formula C-204. |
| BC-P21-(O-AEEAc)$_x$-MET4-8-(O-AEEAc)$_y$-P21 | Formula C-205. |
| BC-P21-(O-dPEG21)$_x$-MET4-8 | Formula C-206. |

For structural formulas C-1 to C-102 and C-105 to C-206 above, x is 1, 2, 3, 4, 5, 6, 7, 8, 9, or 10; and y is 1, 2, 3, 4, 5, 6, 7, 8, 9, or 10. Bonding can occur at either end, or in any position, of MET12, MET4-8, P6, P21, or BC. For example, "P6-MET12" indicates both P6-MET12 and MET12-P6 P6, MET12, GGG, N-AEEAc, N-dPEG12, etc., represent the corresponding compound with the structure modified to accommodate the bonding represented. For example, P6 is Ac-VGDGGLFEKKL-NH$_2$ (SEQ ID NO: 1).

MET12 is (SEQ ID NO: 3)

HHIYLGAVNYI—NH—CH(CH$_2$-C$_6$H$_4$-OH)—COOH

One potential structure for P6-MET12 (P6 and MET12 disclosed as SEQ ID NOS 1 and 3, respectively) is:

HHIYLGAVNYI—NH—CH(CH$_2$-C$_6$H$_4$-OH)—C(=O)—NH—Ac-VGDGGLFEKKL

Some covalent linked compounds for use in a drug delivery system include:

Formula C103

Formula C104

With respect to any relevant structural representation, such as Formula C103 or C104, z is 0-10,000, 0-1,000, 1,000-2,000, 2,000-3,000, 3,000-4,000, 4,000-5,000, 5,000-6,000, 6,000-7,000, 8,000-9,000, 9,000-10,000, 0-5,000, or 5,000-10,000.

With respect to any relevant structural representation, such as Formula C104, Y is N or O.

With respect to any relevant structural representation, such as Formula C104, $A^1$ is P6, P21, or a group derived from C1-C34, e.g. with the relevant atoms removed to accommodate the bonding, as explained above.

With respect to any relevant structural representation, such as Formula C104, $A^2$ is —OCH$_2$CH$_2$O— or —NHCH$_2$CH$_2$N—.

Some examples of bimatoprost acid covalently linked to MET4-8 (e.g. MET4, MET5, MET6, MET7 or MET8), MET12, P6, or P21 are represented by Formula C207:

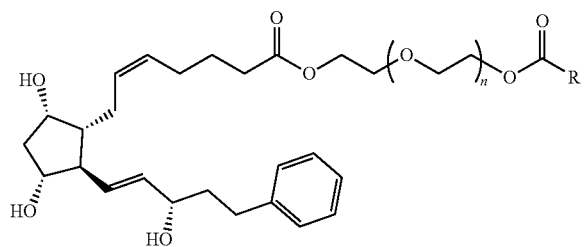

Formula C-207 wherein n is about 2-2,000, such as 2, 3, 4, 5, 6, 7, 8, 9, 10, 10-20, 20-30, 30-40, 40-50, 50-60, 60-70, 70-80, 80-90, 90-100, 2-30, 30-60, 60-100, 100-200, 200-300, 300-400, 400-500, 500-600, 600-700, 700-800, 800-900, 900-1,000, 1,000-1,100, 1,100-1,200, 1,200-1,300, 1,300-1,400, 1,400-1,500, 1,500-1,600, 1,600-1,700, 1,700-1,800, 1,800-1,900, 1,900-2,000, 2-500, 500-1,000, 2-1,000, 1,000-1,500, 1,500-2,000, or 1,000-2,000; and R—H is MET4-8 (e.g. MET4, MET5, MET6, MET7 or MET8), MET12, P6, or P21.

For example, bimatoprost acid covalently linked to MET4 may be represented by Formula C-208:

2 months, at least about 3 months, at least about 4 months, at least about 5 months, at least about 6 months, at least about 9 months, at least about 12 months, at least about 18 months, at least about 2 years, at least about 3 years, at least about 5 years, or longer. Typically, a sustained delivery component is an implant, such as a solid implant, that works by encapsulating or otherwise entrapping the drug into the implant. If the implant is biodegradable or bioerodible, the drug may be released as the implant biodegrades or bioerodes. The implant may also be porous so that, over a period of time, drug may diffuse out of the implant. Biodegradable or bioerodible implants may be porous or non-porous. Typically, non-biodegradable or non-bioerodible implants are porous, and the drug is released by diffusion. However, other mechanisms may operate, such as an osmotic pump.

In some embodiments, the drug delivery system may be implanted into the mammal, such as a human being, at an interval of about 1 week to about 10 years, about 1-12 weeks, about 3-6 months, about 6-9 months, about 9-12 months, about 12-18 months, about 18-24 months, about 0.1-3 years, about 3-5 years, or about 5-10 years.

In some embodiments, a treatment effect, such as reduced intraocular pressure or reduced vision loss, may be observed for at least about 1 week, at least about 2 weeks, at least about 3 weeks, at least about 1 month, at least about 2 months, at least about 3 months, at least about 4 months, at least about 5 months, at least about 6 months, at least about 9 months, at least about 12 months, at least about 18 months, at least about 2 years, at least about 3 years, at least about 5 years, about 1 week to about 10 years, about 1-12 weeks, about 3-6 months, about 6-9 months, about 9-12 months, about 12-18 months, about 18-24 months, about 0.1-3 years, about 3-5 years, about 5-10 years, or longer, after the drug delivery system is implanted into a mammal, such as a human being.

The drug may be physically trapped in the sustained delivery component and/or may be covalently bonded to a molecule that is part of the sustained delivery component.

Typical examples of biodegradable materials for porous or non-porous biodegradable implants generally include,

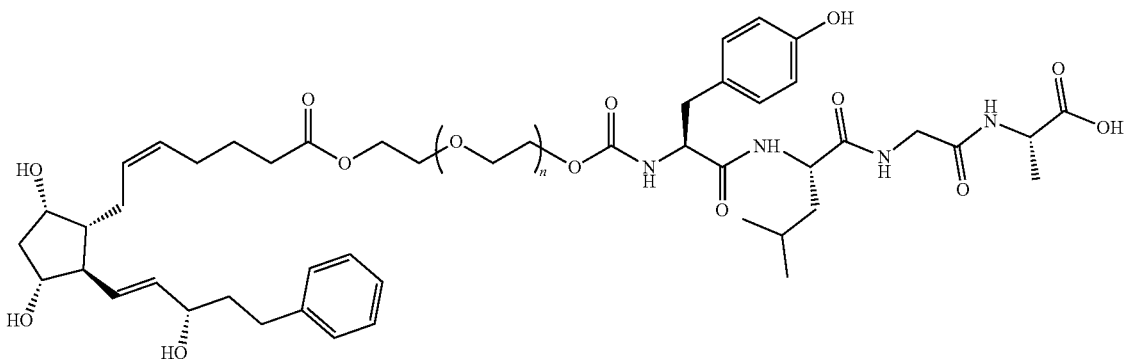

Formula C-208

A sustained delivery component is the portion of the drug delivery system that allows the drug to remain in the body for a sustained period of time, e.g. long beyond the time that it takes for the drug to be metabolized or passed out of the body, such as at least about 1 week, at least about 2 weeks, at least about 3 weeks, at least about 1 month, at least about silica-based materials, or organic biodegradable materials, such as polymers comprising poly (D,L-lactic acid) (PLA) and poly (D,L-lactic-co-glycolic acid)(PLGA), polyester-amide (PEA, DSM chemical), and polycaprolactone (PCL); hydrogels, such as polyvinyl alcohols (PVA), PEG amines, PEG-N-hydroxysuccinamide esters (like Ocular Therapeutix) and the like; collagen based materials (e.g. Euclid systems); or a combination thereof.

There are a number of suitable silica based sustained delivery components.

One type of silica based sustained delivery component includes a silica hydrogel composite obtainable by mixing silica particles, comprising an encapsulated drug, with a silica sol, wherein obtained hydrogel composite is shear-thinning. This type of delivery system is an injectable, all-silica-based microparticle-silica hydrogel controlled release system which reduces the burst remarkably with different types of encapsulated therapeutic and biologically active agents. Detailed descriptions of this type of silica based sustained delivery component, and how they are made, are found in U.S. Pat. No. 9,949,922, issued on Apr. 24, 2018 to Jokinen, et al., which is incorporated by reference herein in its entirety.

Another type of silica based sustained delivery component includes flowing silica compositions and gels comprising a drug which are obtainable by method for producing a flowing silica composition including a sol-gel transfer, where redispersion is carried out. The redispersion includes adding, after having reached gel point of the sol-gel transfer, liquid into the gel formed by the sol-gel transfer, and the addition being made within a sufficiently short time period after reaching the gel point, to result, after mixing of the gel and the liquid, in a rheologically homogenous flowing silica composition, which is and remains injectable as such, or by short stirring <30 s, through a thin 22G needle. These flowing and injectable sustained delivery silica compositions may increase the stability and preserve the activity of encapsulated therapeutic agents. Detailed descriptions of this type of silica based sustained delivery component, and how it is made, is found in United States Patent Application No. 20140057996, published Feb. 27, 2014 by Jokinen, et al., which is incorporated by reference herein in its entirety.

Another type of silica based sustained delivery component comprises a composition comprising a bioerodible porous silicon-based carrier material wherein the carrier material carries a drug and at least one amorphous sugar, optionally further comprising a crystallization inhibitor. These delivery systems comprise loading biomolecules into the pores of the silica carrier material, thus stabilizing the biomolecules. However, these systems may also be used for small molecule therapeutic compounds. Detailed descriptions of this type of silica based sustained delivery component, and how it is made, is found in U.S. Pat. No. 9,603,801, issued on Mar. 28, 2017 to Barnett, et al., which is incorporated by reference herein in its entirety.

Another type of silica based sustained delivery component includes bioerodible devices, such as implants for delivering drugs in a controlled manner. The devices comprise a porous silicon-based carrier material impregnated or loaded with the drug. These particular silicon carrier materials comprise at least one large molecule therapeutic agent disposed in the pores of the carrier material. It is believed that the loading of large therapeutic molecule into the pores of the carrier material stabilizes the large molecules. In many embodiments, the large molecule is a protein and the pores have an average size between about 15 nm to about 40 nm, and the protein has a molecular weight from about 100,000 amu to about 200,000 amu. However, these systems may also be used for small molecule therapeutic compounds. Detailed descriptions of this type of silica based sustained delivery component, and how it is made, is found in U.S. Pat. No. 9,808,421, issued on Nov. 7, 2017, to Ashton et al., U.S. Pat. No. 9,333,173 issued on May 10, 2016 to Ashton et al., and United States Patent Publication No. 20140271764 published on Sep. 28, 2014 by Ashton, et al., all of which are incorporated by reference herein in its entirety.

The sustained delivery component may have any suitable mass, such as about 10 μg-100 mg, about 10-20 μg, about 20-30 μg, about 30-40 μg, about 40-50 μg, about 50-60 μg, about 60-70 μg, about 70-80 μg, about 80-90 μg, about 90-100 μg, about 100-200 μg, about 200-300 μg, about 300-400 μg, about 400-500 μg, about 500-600 μg, about 600-700 μg, about 700-800 μg, about 800-900 μg, about 900-1,000 μg, about 1-2 mg, about 2-3 mg, about 3-4 mg, about 4-5 mg, about 5-6 mg, about 6-7 mg, about 7-8 mg, about 8-9 mg, about 9-10 mg, about 10-20 mg, about 20-30 mg, about 30-40 mg, about 40-50 mg, about 50-60 mg, about 60-70 mg, about 70-80 mg, about 80-90 mg, about 90-100 mg, about 100-200 mg, about 200-300 mg, about 300-400 mg, about 400-500 mg, about 500-600 mg, about 600-700 mg, about 700-800 mg, about 800-900 mg, about 900-1,000 mg, about 1-2 g, about 2-3 g, about 3-4 g, about 4-5 g, about 5-6 g, about 6-7 g, about 7-8 g, about 8-9 g, about 9-10 g, about 10-20 g, about 20-30 g, about 30-40 g, about 40-50 g, about 50-60 g, about 60-70 g, about 70-80 g, about 80-90 g, about 90-100 g, about 100-200 g, about 200-300 g, about 300-400 g, about 400-500 g, about 500-600 g, about 600-700 g, about 700-800 g, about 800-900 g, about 900-1,000 g, about 10-100 μg, about 100-1,000 μg, about 1-10 mg, about 10-100 mg, about 100-1,000 mg, about 1-10 g, about 10-100 g, or about 100-1,000 g. Ranges above which are about 1 g or less, or 100 mg or less, may be of interest for drug delivery systems delivered onto or into the eye.

The sustained delivery component may be any suitable percentage of the implant, such as about 1-99 wt %, about 1-10 wt %, about 10-20 wt %, about 20-30 wt %, about 30-40 wt %, about 40-50 wt %, about 50-60 wt %, about 60-70 wt %, about 70-80 wt %, about 80-90 wt %, about 90-99 wt %, about 1-30 wt %, about 30-65 wt %, about 65-99 wt %, about 1-50 wt %, or about 50-99 wt %.

The drug delivery system may be of any suitable size, such as about 10 μg-100 mg, about 10-20 μg, about 20-30 μg, about 30-40 μg, about 40-50 μg, about 50-60 μg, about 60-70 μg, about 70-80 μg, about 80-90 μg, about 90-100 μg, about 100-200 μg, about 200-300 μg, about 300-400 μg, about 400-500 μg, about 500-600 μg, about 600-700 μg, about 700-800 μg, about 800-900 μg, about 900-1,000 μg, about 1-2 mg, about 2-3 mg, about 3-4 mg, about 4-5 mg, about 5-6 mg, about 6-7 mg, about 7-8 mg, about 8-9 mg, about 9-10 mg, about 10-20 mg, about 20-30 mg, about 30-40 mg, about 40-50 mg, about 50-60 mg, about 60-70 mg, about 70-80 mg, about 80-90 mg, about 90-100 mg, about 100-200 mg, about 200-300 mg, about 300-400 mg, about 400-500 mg, about 500-600 mg, about 600-700 mg, about 700-800 mg, about 800-900 mg, about 900-1,000 mg, about 1-2 g, about 2-3 g, about 3-4 g, about 4-5 g, about 5-6 g, about 6-7 g, about 7-8 g, about 8-9 g, about 9-10 g, about 10-20 g, about 20-30 g, about 30-40 g, about 40-50 g, about 50-60 g, about 60-70 g, about 70-80 g, about 80-90 g, about 90-100 g, about 100-200 g, about 200-300 g, about 300-400 g, about 400-500 g, about 500-600 g, about 600-700 g, about 700-800 g, about 800-900 g, about 900-1,000 g, about 10-100 μg, about 100-1,000 μg, about 1-10 mg, about 10-100 mg, about 100-1,000 mg, about 1-10 g, about 10-100 g, or about 100-1,000 g. Ranges above which are about 1 g or less, or 100 mg or less, may be of interest for drug delivery systems delivered onto or into the eye.

Typical examples of non-biodegradable or non-bioerodible materials for implants include silicones or PVA as semipermeable membranes (like Psivida).

Other potential sustained delivery components could be based upon cell-based approaches like encapsulated cell technology; and reservoir type approaches (forsight4; Replenish).

The prostaglandin compound or prostaglandin receptor agonist, the intraocular pressure lowering agent, and/or the neurotrophic agent, such as the CNTF compound, may, or may not, be covalently attached to the sustained delivery component.

In some embodiments, the prostaglandin compound or prostaglandin receptor agonist is covalently attached to the sustained delivery component. In some embodiments, the prostaglandin compound or prostaglandin receptor agonist is not covalently attached to the sustained delivery component.

In some embodiments, the intraocular pressure lowering agent is covalently attached to the sustained delivery component. In some embodiments, the intraocular pressure lowering agent is not covalently attached to the sustained delivery component.

In some embodiments, the neurotrophic agent, such as the CNTF compound, is covalently attached to the sustained delivery component. In some embodiments, the neurotrophic agent, such as the CNTF compound, is not covalently attached to the sustained delivery component.

For example, a prostaglandin compound or prostaglandin receptor agonist may be covalently attached to the sustained delivery component using a compound represented by a formula:

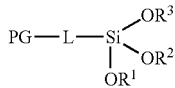

Formula 3 wherein PG-H is a prostaglandin compound or prostaglandin receptor agonist, such as a prostaglandin compound or prostaglandin receptor agonist recited above.

Compounds of Formula 3 may be further represented by Formula 3A and 3B:

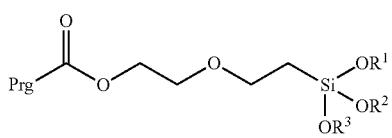

Formula 3A

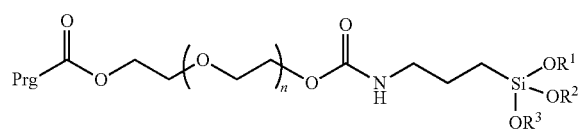

Formula 3B wherein Prg-CO$_2$H is a prostaglandin agonist and n is 1, 2, 3, 4, 5, 6, 7, 8, 9, 10, etc.

An intraocular pressure lowering agent may be covalently attached to the sustained delivery component using a compound represented by a formula:

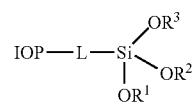

Formula 4 wherein IOP-H is an intraocular pressure lowering agent, such as an intraocular pressure lowering agent recited above.

A CNTF compound or another neurotrophic agent may be covalently attached to the sustained delivery component using a compound represented by a formula:

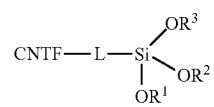

Formula 5 wherein CNTF-H is a CNTF compound or another neurotrophic agent, such as a CNTF compound or another neurotrophic agent recited above.

A CNP compound may be covalently attached to the sustained delivery component using a compound represented by a formula:

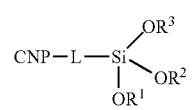

Formula 6 wherein CNP-H is a CNP compound.

An NPR-B compound may be covalently attached to the sustained delivery component using a compound represented by a formula:

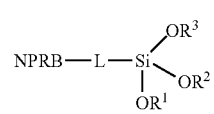

Formula 7 wherein NPRB-H is an NRP-B compound.

With respect to any relevant structural representation, such as Formula 3, 3A, 3B, 4, 5, 6, or 7, or the compounds depicted below, $R^1$ is independently H or $C_{1-6}$ alkyl, such as $CH_3$, $C_2$ alkyl, $C_3$ alkyl, $C_4$ alkyl, $C_5$ alkyl, or $C_6$ alkyl.

With respect to any relevant structural representation, such as Formula 3, 3A, 3B, 4, 5, 6, or 7, or the compounds depicted below, re is independently H or $C_{1-6}$ alkyl, such as $CH_3$, $C_2$ alkyl, $C_3$ alkyl, $C_4$ alkyl, $C_5$ alkyl, or $C_6$ alkyl.

With respect to any relevant structural representation, such as Formula 3, 3A, 3B, 4, 5, 6, or 7, or the compounds depicted below, and $R^3$ is independently H or $C_{1-6}$ alkyl, such as $CH_3$, $C_2$ alkyl, $C_3$ alkyl, $C_4$ alkyl, $C_5$ alkyl, or $C_6$ alkyl.

The compounds are examples of compounds of Formula 3, 3A or 3B:

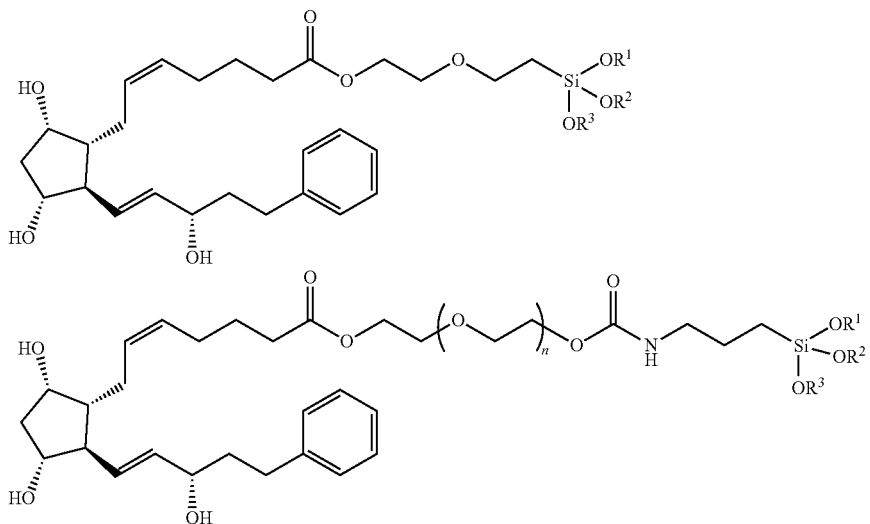
In the body, the ester bond can hydrolyze to release the compound:
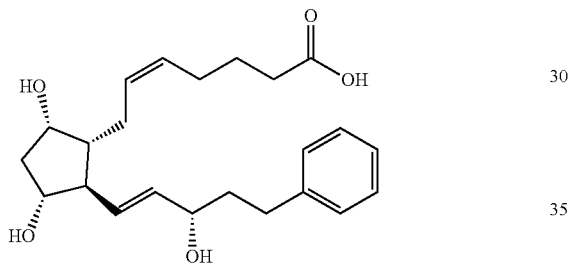
The table below shows three compounds that are examples of compounds of Formula 4, and the three compounds that can be released in the body by hydrolysis of the ester or amide group:
| Compound of Formula 4 | Compound released in body |
|---|---|

| Compound of Formula 4 | Compound released in body |
|---|---|
| 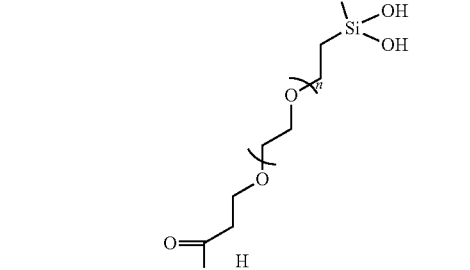 | 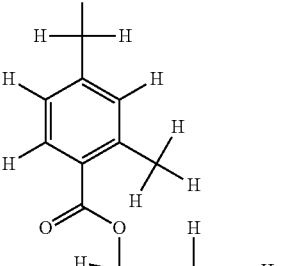 |

In the table above, any $Si(OH)_3$ group may be replaced with $SiOR^1OR^2OR^3$.

An example of a compound of Formula 5 is: VGDG-GLFEKKL-PEG-Si(OH)$_3$ ("VGDGGLFEKKL" disclosed as SEQ ID NO: 1) or VGDGGLFEKKL-PEG-SiOR$^1$OR$^2$OR$^3$ ("VGDGGLFEKKL" disclosed as SEQ ID NO: 1) wherein PEG is a polyethylene glycol chain (e.g. $(OCH_2CH_2)_n$—, where n is 1, 2, 3, 4, 5, 6, 7, 8, 9, 10, etc.). In the body, the ester bond can hydrolyze to release VGDG-GLFEKKL (SEQ ID NO: 1).

The SiOR$^1$OR$^2$OR$^3$ group of Formulas 3, 3A, 3B, 4, 5, 6, or 7 may be covalently bonded to the silica of a silica based drug delivery system, e.g. to form compounds represented by Formulas 3D, 3AD, 3BD, 4D, or 5D, wherein D is a sustained delivery component comprising the Si of the SiOR$^1$OR$^2$OR$^3$ of Formula 3, 3A, 3B, 4, 5, 6, or 7.

PG—L—D     Formula 3D

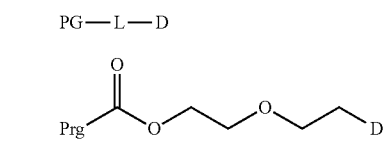

Formula 3AD

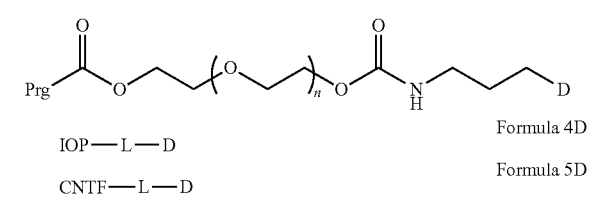

Formula 3BD

IOP—L—D     Formula 4D

CNTF—L—D     Formula 5D

Some drug delivery systems may be comprise a polymer represented by a formula:

$$\begin{array}{c} OX \\ | \\ \sim\!\!-O-Si-O-Si-O-Si-\!\!\sim \\ | \quad\quad | \quad\quad | \\ OX \quad OX \quad OX \end{array}$$

wherein each X is independently

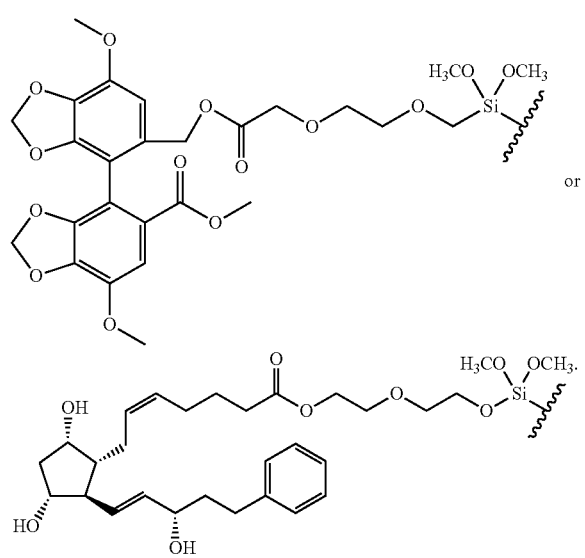

A subject drug delivery system may be administered to a mammal, such as a human, by any suitable method, such as by injection or surgical implantation into any part of the body, oral administration, or topical application to the eye or skin. In some embodiments, an implant is injected or otherwise implanted in or around an eye, including but not limited to: the anterior chamber, the vitreous, the posterior chamber, the subconjunctival space, the suprachoroidal space, or subtenon's space.

A subject drug delivery system may extend the amount of time that the drug remains in the body. For example, a drug delivery system may provide therapeutic levels of the drug for at least about 2 weeks, at least about 4 weeks, at least about 6 weeks, at least about 8 weeks, at least about 3 months, at least about 4 months, at least about 5 months, at least about 6 months, at least about 7 months, at least about 8 months, at least about 9 months, at least about 10 months, at least about 11 months, at least about 1 year, at least about 1.5 years, at least about 2 years, at least about 3 years, at least about 4 years, about 1-6 months, about 6-12 months, about 12-18 months, about 18-24 months, about 24-36 months, up to about 2 years, up to about 3 years, up to about 4 years, up to about 5 years, or up to about 10 years. The drug delivery system may be injected, implanted, or changed at a time in any of the ranges above.

In some embodiments, a subject drug delivery system may be administered to a mammal, such as a human being, to treat a glaucoma, such as Primary Open-Angle Glaucoma (POAG), Acute Primary Angle Close Glaucoma (APACG), Chronic Angle Closure Glaucoma, Pigmentary Glaucoma, Pseudoexfoliation Glaucoma, Normal Tension Glaucoma, Pediatric Glaucoma, a secondary glaucoma, etc., or a combination thereof.

EXAMPLES

The following examples are intended to be illustrative of the embodiments of the disclosure, but are not intended to limit the scope or underlying principles in any way.

Example 1: Solid Phase Synthesis of a PG-L-CNTF Featuring an Amide Linkage

Using methods known in the art, peptide 6 is linked to a resin at the $NH_2$ terminus, is protected with BOC groups and t-Bu ester groups, and linked to $NH_2$-terminated-PEG at the carboxylic acid terminus to provide Resin-L-K(Boc)-K(Boc)-E(tBu)-F-L-G-G-D(tBu)-G-V—$CO_2(CH_2$—$CH_2$—$O)_n$—$CH_2$—$CH_2$—$NH_2$ (SEQ ID NO: 18). The nature of the starting materials, and the order of reactions may be modified to improve efficiency and selectivity, and all reactions are conducted using methods known in the art. Bimatoprost free acid, having its three hydroxyl groups protected with t-butyl groups (or other alkyl- or silyl-protecting groups, as appropriate), is prepared by methods known in the art. The free amine of the protected peptide 6 compound and the free acid of the protected prostaglandin compound may be coupled by any appropriate peptide coupling method known in the art. Following the coupling reaction, the protected amide can be fully deprotected using TFA or other acid-catalyzed methods know in the art to release the Peptide 6-Linker-Bimatoprost amide derivative. Different orthogonal protecting group strategies may be employed as necessary, as known in the art, to optimize the efficiency of the overall procedure.

Example 2: Solid Phase Synthesis of a PG-L-CNTF Featuring an Ester Linkage

Using methods known in the art, peptide 6 is linked to a resin at the $NH_2$ terminus, is protected with CBz groups on the free amine groups and benzyl groups on the free acid groups, and is coupled to polyethylene glycol at the carboxylic acid terminus to provide Resin-L-K(Cbz)-K(Cbz)-E(Bn)-F-L-G-G-D(Bn)-G-V—$CO_2(CH_2$—$CH_2$—$O)_n$—$CH_2$—$CH_2$—OH (SEQ ID NO: 19). The nature of the starting materials and the order of reactions may be modified to improve selectivity, and all reactions are conducted using methods known in the art. Bimatoprost free acid, having its three hydroxyl groups protected with benzyl groups (or other hydrogenation-labile protecting groups, as appropriate), is prepared by methods known in the art. The free alcohol terminus of the protected peptide 6 compound and the free acid of the protected prostaglandin compound may be coupled by any appropriate ester coupling method known in the art. Following the coupling reaction, the protected ester can be fully deprotected using hydrogenation methods or other debenzylation methods known in the art to release the Peptide 6-Linker-Bimatoprost ester derivative. Different orthogonal protecting group strategies may be employed as necessary, as known in the art, to optimize the efficiency of the overall procedure.

Example 3

Eight African Green monkeys were screened to identify 4 animals with high-normal IOP. Animals were anesthetized with ketamine 10 mg/kg and Xylazine 0.5 mg/kg. Bimatoprost acid 100 ng in 50 µl was injected intravitreally in one eye through a 30-gauge syringe using a shelved technique, and 50 µl of phosphate buffered saline (PBS) was injected into the fellow eye as a concurrent control on days 0, 1, 2 at 8:30 pm. The bimatoprost acid dose was escalated to 200 ng in 100 µl, with the same volume of PBS given to the fellow eye, on days 3 (8:30 pm) and 4 (5:30 pm). IOP was measured with a Tonovet tonometer at 8:30 am, 11:30 am and 8:30 pm on day 1; 8:30 am, 11:30 am and 5:30 pm on day 4; and at 8:30 am on days 2, 3 and 5. The person measuring the IOP was masked to treatment assignment. Slit lamp exams were performed on day 0, 1 and 5. OCTs were performed at baseline and day 5.

Figure 2:
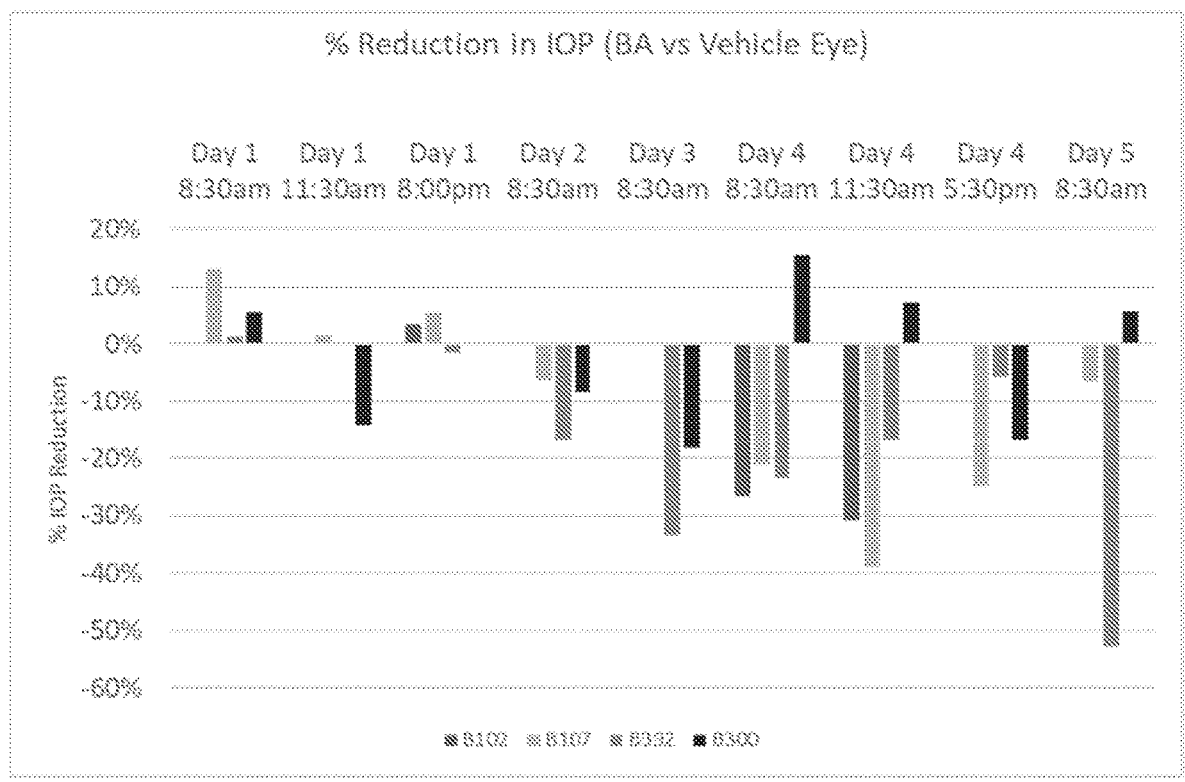
FIG. 2 is the percent reduction in intraocular pressure of African Green Monkeys IOP following administration of 100 ng and 200 ng bimatoprost acid by intravitreal injection compared with PBS in the fellow eye as related to some embodiments described herein.

One of four animals (B392) responded to the 100 ng dose with a reduction in IOP of ≥30% (the typical effect of prostaglandin analogs on IOP) when compared with the fellow eye at 1 timepoint. Three of four animals responded to the 200 ng dose with a reduction in IOP of ≥30% at 1 or more timepoints, with the IOP in one animal (B392) reduced by 52% on day 5 in the treated eye compared with the fellow eye receiving PBS. Notably, this was the same animal that responded to the 100 ng dose suggesting that this animal was more responsive to bimatoprost acid than the others. The time course of IOP reduction is consistent with the short half-life of bimatoprost when injected by bolus injection into the eye. One animal (B300) did not respond to either dose. The actual IOP measurements and the percent reductions in IOP are presented in FIGS. 1 and 2, respectively.

Clinical examination revealed no ocular inflammation, but one animal experienced corneal edema deemed to be related to the multiple procedures and not drug-related. OCTs showed no cystoid macular edema in any animal.

These results demonstrate a clear IOP lowering-effect of intravitreal bimatoprost acid with a dose-response between the 100 ng and 200 ng doses. As no ocular inflammation was observed, this is an unlikely cause of IOP reduction in the treated eyes. Moreover, this study was masked and controlled with vehicle injections given concurrently in the fellow eye using the same volumes. Therefore, the IOP results are unlikely to be procedure-related (e.g., wound leak) as significant IOP reduction was only seen in the treated eyes. Further escalation in dose is expected to have an even greater IOP-lowering effect. The test article was well-tolerated.

Based on these results, a sustained delivery form of intravitreal bimatoprost acid would be expected to safely achieve clinically meaningful IOP lowering in patients.

The following embodiments are specifically contemplated by the inventors:

Embodiment 1. A drug delivery system comprising an intraocular pressure lowering agent, a neurotrophic agent, a C-type Natriuretic Peptide (CNP), a Natriuretic Peptide Receptor-B (NPR-B), or an apoptosis signaling fragment inhibitor (FAS) or FAS-ligand (FASL) inhibitor, and a sustained delivery component.

Embodiment 2. The drug delivery system of Embodiment 1, comprising the intraocular pressure lowering agent.

Embodiment 3. The drug delivery system of Embodiment 2, wherein the intraocular pressure lowering agent is a prostaglandin compound.

Embodiment 4. The drug delivery system of Embodiment 2 or 3, further comprising a second intraocular pressure lowering agent.

Embodiment 5. The drug delivery system of Embodiment 2, 3, or 4, wherein the intraocular pressure lowering agent comprises a beta blocker.

Embodiment 6. The drug delivery system of Embodiment 2, 3, 4, or 5, wherein the intraocular pressure lowering agent comprises timolol.

Embodiment 7. The drug delivery system of Embodiment 2, 3, 4, 5, or 6, wherein the intraocular pressure lowering agent comprises betaxolol.

Embodiment 8. The drug delivery system of Embodiment 2, 3, 4, 5, 6, or 7, wherein the intraocular pressure lowering agent comprises levobunolol.

Embodiment 9. The drug delivery system of Embodiment 2, 3, 4, 5, 6, 7, or 8, wherein the intraocular pressure lowering agent comprises metipranolol.

Embodiment 10. The drug delivery system of Embodiment 2, 3, 4, 5, 6, 7, 8, or 9, wherein the intraocular pressure lowering agent comprises an alpha adrenergic agonist.

Embodiment 11. The drug delivery system of Embodiment 2, 3, 4, 5, 6, 7, 8, 9, or 10, wherein the intraocular pressure lowering agent comprises brimonidine.

Embodiment 12. The drug delivery system of Embodiment 2, 3, 4, 5, 6, 7, 8, 9, 10, or 11, or 10, wherein the intraocular pressure lowering agent comprises apraclonidine.

Embodiment 13. The drug delivery system of Embodiment 2, 3, 4, 5, 6, 7, 8, 9, 10, 11, or 12, wherein the intraocular pressure lowering agent comprises a carbonic anhydrase inhibitor.

Embodiment 14. The drug delivery system of Embodiment 2, 3, 4, 5, 6, 7, 8, 9, 10, 11, 12, or 13, wherein the intraocular pressure lowering agent comprises brinzolamide.

Embodiment 15. The drug delivery system of Embodiment 2, 3, 4, 5, 6, 7, 8, 9, 10, 11, 12, 13, or 14, wherein the intraocular pressure lowering agent comprises acetazolamide.

Embodiment 16. The drug delivery system of Embodiment 2, 3, 4, 5, 6, 7, 8, 9, 10, 11, 12, 13, 14, or 15, wherein the intraocular pressure lowering agent comprises dorzolamide.

Embodiment 17. The drug delivery system of Embodiment 2, 3, 4, 5, 6, 7, 8, 9, 10, 11, 12, 13, 14, 15, or 16, wherein the intraocular pressure lowering agent comprises methazolamide.

Embodiment 18. The drug delivery system of Embodiment 2, 3, 4, 5, 6, 7, 8, 9, 10, 11, 12, 13, 14, 15, 16, or 17, wherein the intraocular pressure lowering agent comprises a cholinergic.

Embodiment 19. The drug delivery system of Embodiment 2, 3, 4, 5, 6, 7, 8, 9, 10, 11, 12, 13, 14, 15, 16, 17, or 18, wherein the intraocular pressure lowering agent comprises pilocarpine.

Embodiment 20. The drug delivery system of Embodiment 2, 3, 4, 5, 6, 7, 8, 9, 10, 11, 12, 13, 14, 15, 16, 17, 18, or 19, wherein the intraocular pressure lowering agent comprises carbachol.

Embodiment 21. The drug delivery system of Embodiment 2, 3, 4, 5, 6, 7, 8, 9, 10, 11, 12, 13, 14, 15, 16, 17, 18, 19, or 20, wherein the intraocular pressure lowering agent comprises a Rho Kinase (ROCK) inhibitor.

Embodiment 22. The drug delivery system of Embodiment 2, 3, 4, 5, 6, 7, 8, 9, 10, 11, 12, 13, 14, 15, 16, 17, 18, 19, 20, or 21, wherein the intraocular pressure lowering agent comprises netarsudil.

Embodiment 23. The drug delivery system of Embodiment 1, 2, 3, 4, 5, 6, 7, 8, 9, 10, 11, 12, 13, 14, 15, 16, 17, 18, 19, 20, 21, or 22, comprising the neurotrophic agent.

Embodiment 24. The drug delivery system of Embodiment 1, 2, 3, 4, 5, 6, 7, 8, 9, 10, 11, 12, 13, 14, 15, 16, 17, 18, 19, 20, 21, 22, or 23, comprising both the prostaglandin receptor agonist and the neurotrophic agent.

Embodiment 25. The drug delivery system of Embodiment 24, wherein the prostaglandin receptor agonist and the neurotrophic agent are covalently bound to one another.

Embodiment 26. The drug delivery system of Embodiment 25, wherein the prostaglandin receptor agonist and the neurotrophic agent are covalently bound to one another via a linking group.

Embodiment 27. The drug delivery system of Embodiment 3, 4, 5, 6, 7, 8, 9, 10, 11, 12, 13, 14, 15, 16, 17, 18, 19, 20, 21, 22, 23, 24, 25, or 26, wherein the prostaglandin receptor agonist comprises bimatoprost.

Embodiment 28. The drug delivery system of Embodiment 3, 4, 5, 6, 7, 8, 9, 10, 11, 12, 13, 14, 15, 16, 17, 18, 19, 20, 21, 22, 23, 24, 25, or 26, wherein the prostaglandin receptor agonist comprises travoprost.

Embodiment 29. The drug delivery system of Embodiment 3, 4, 5, 6, 7, 8, 9, 10, 11, 12, 13, 14, 15, 16, 17, 18, 19, 20, 21, 22, 23, 24, 25, or 26, wherein the prostaglandin receptor agonist comprises latanoprost.

Embodiment 30. The drug delivery system of Embodiment 3, 4, 5, 6, 7, 8, 9, 10, 11, 12, 13, 14, 15, 16, 17, 18, 19, 20, 21, 22, 23, 24, 25, or 26, wherein the prostaglandin receptor agonist comprises latanoprostene.

Embodiment 31. The drug delivery system of Embodiment 3, 4, 5, 6, 7, 8, 9, 10, 11, 12, 13, 14, 15, 16, 17, 18, 19, 20, 21, 22, 23, 24, 25, or 26, wherein the prostaglandin receptor agonist comprises tafluprost.

Embodiment 32. The drug delivery system of Embodiment 3, 4, 5, 6, 7, 8, 9, 10, 11, 12, 13, 14, 15, 16, 17, 18, 19, 20, 21, 22, 23, 24, 25, or 26, wherein the prostaglandin receptor agonist comprises a prostaglandin EP2 receptor agonist.

Embodiment 33. The drug delivery system of Embodiment 3, 4, 5, 6, 7, 8, 9, 10, 11, 12, 13, 14, 15, 16, 17, 18, 19, 20, 21, 22, 23, 24, 25, or 26, wherein the prostaglandin receptor agonist comprises a prostaglandin EP3 receptor agonist.

Embodiment 34. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33, wherein the neurotrophic agent comprises CNTF Peptide 6.

Embodiment 35. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34, wherein the neurotrophic agent comprises CNTF Peptide 21.

Embodiment 36. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35, comprising the CNP compound.

Embodiment 37. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36, comprising the NPR-B compound.

Embodiment 38. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37, comprising both the intraocular pressure lowering agent and the neurotrophic agent.

Embodiment 39. The drug delivery system of Embodiment 38, wherein the intraocular pressure lowering agent and the neurotrophic agent are covalently bound to one another.

Embodiment 40. The drug delivery system of Embodiment 39, wherein the intraocular pressure lowering agent and the neurotrophic agent are covalently bound to one another via a linking group.

Embodiment 41. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, comprising both the intraocular pressure lowering agent and the CNP compound.

Embodiment 42. The drug delivery system of Embodiment 41, wherein the intraocular pressure lowering agent and the CNP compound are covalently bound to one another.

Embodiment 43. The drug delivery system of Embodiment 42, wherein the intraocular pressure lowering agent and the CNP compound are covalently bound to one another via a linking group.

Embodiment 44. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43, comprising both the intraocular pressure lowering agent and the NPR-B compound.

Embodiment 45. The drug delivery system of Embodiment 44, wherein the intraocular pressure lowering agent and the NPR-B compound are covalently bound to one another.

Embodiment 46. The drug delivery system of Embodiment 45, wherein the intraocular pressure lowering agent and the NPR-B compound are covalently bound to one another via a linking group.

Embodiment 47. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46, comprising both the neurotrophic agent and the CNP compound.

Embodiment 48. The drug delivery system of Embodiment 47, wherein the neurotrophic agent and the CNP compound are covalently bound to one another.

Embodiment 49. The drug delivery system of Embodiment 48 wherein the neurotrophic agent and the CNP compound are covalently bound to one another via a linking group.

Embodiment 50. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49, comprising both the neurotrophic agent and the NPR-B compound.

Embodiment 51. The drug delivery system of Embodiment 50, wherein the neurotrophic agent and the NPR-B compound are covalently bound to one another.

Embodiment 52. The drug delivery system of Embodiment 51, wherein the neurotrophic agent and the NPR-B compound are covalently bound to one another via a linking group.

Embodiment 53. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, comprising both the CNP compound and the NPR-B compound.

Embodiment 54. The drug delivery system of Embodiment 53, wherein the CNP compound and the NPR-B compound are covalently bound to one another.

Embodiment 55. The drug delivery system of Embodiment 54, wherein the CNP compound and the NPR-B compound are covalently bound to one another via a linking group.

Embodiment 56. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55, wherein the neurotrophic agent is a CNTF compound.

Embodiment 57. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56, wherein the sustained delivery component is silica based.

Embodiment 58. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56, wherein the sustained delivery component is porous.

Embodiment 59. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56, wherein the sustained delivery component is non-porous.

Embodiment 60. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56, wherein the sustained delivery component is of the type described in U.S. Pat. No. 9,949,922, issued on Apr. 24, 2018 to Jokinen, et al.

Embodiment 61. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56, wherein the sustained delivery component is of the type described in United States Patent Application Publication No. 20140057996, published Feb. 27, 2014 by Jokinen, et al.

Embodiment 62. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56, wherein the sustained delivery component is of the type described in U.S. Pat. No. 9,603,801, issued on Mar. 28, 2017 to Barnett, et al.

Embodiment 63. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56, wherein the sustained delivery component is of the type described in U.S. Pat. No. 9,808,421, issued on Nov. 7, 2017, to Ashton et al.

Embodiment 64. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56, wherein the sustained delivery component is of the type described in U.S. Pat. No. 9,333,173 issued on May 10, 2016 to Ashton et al.

Embodiment 65. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56, wherein the sustained delivery component is of the type described in United States Patent Publication No. 20140271764 published on Sep. 28, 2014 by Ashton, et al.

Embodiment 66. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65, wherein the prostaglandin receptor agonist is covalently attached to the sustained delivery component.

Embodiment 67. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 66, wherein the neurotrophic agent is covalently attached to the sustained delivery component.

Embodiment 68. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or 67, wherein the prostaglandin receptor agonist is not covalently attached to the sustained delivery component.

Embodiment 69. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, or 68 wherein the neurotrophic agent is not covalently attached to the sustained delivery component.

Embodiment 70. A method of treating a glaucoma or ocular hypertension comprising administering a drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 to a mammal suffering from glaucoma or ocular hypertension.

Embodiment 71. The method of Embodiment 70, wherein the drug delivery system is administered by intravitreal injection into an affected eye of the mammal.

Embodiment 72. The method of Embodiment 70, wherein the drug delivery system is implanted into the anterior chamber, the subconjunctival space, the suprachoroidal space, or the subtenon's space of an affected eye of the mammal.

Embodiment 73. The method of Embodiment 70, 71, or 72, wherein the glaucoma comprises Primary Open-Angle Glaucoma (POAG).

Embodiment 74. The method of Embodiment 70, 71, or 72, wherein the glaucoma comprises Acute Primary Angle Close Glaucoma (APACG).

Embodiment 75. The method of Embodiment 70, 71, or 72, wherein the glaucoma comprises Chronic Angle Closure Glaucoma.

Embodiment 76. The method of Embodiment 70, 71, or 72, wherein the glaucoma comprises Pigmentary Glaucoma.

Embodiment 77. The method of Embodiment 70, 71, or 72, wherein the glaucoma comprises Pseudoexfoliation Glaucoma.

Embodiment 78. The method of Embodiment 70, 71, or 72, wherein the glaucoma comprises Normal Tension Glaucoma.

Embodiment 79. The method of Embodiment 70, 71, or 72, wherein the glaucoma comprises Pediatric Glaucoma.

Embodiment 80. The method of Embodiment 70, 71, or 72, wherein the glaucoma comprises a secondary glaucoma.

Embodiment 81. A drug delivery system comprising: a first active pharmaceutical ingredient (API) and a sustained delivery component, wherein the first API is an intraocular pressure lowering agent, a neurotrophic agent, a C-type Natriuretic Peptide (CNP), a Natriuretic Peptide Receptor-B (NPR-B), an apoptosis signaling fragment (FAS) inhibitor or a FAS-ligand (FASL) inhibitor, or a combination thereof.

Embodiment 82. The drug delivery system of Embodiment 81, further comprising a second API, wherein the first API is the intraocular pressure lowering agent and the second API is the neurotrophic agent.

Embodiment 83. The drug delivery system of Embodiment 81, further comprising a second API, wherein the first API is the intraocular pressure lowering agent and the second API is the CNP.

Embodiment 84. The drug delivery system of Embodiment 81, further comprising a second API, wherein the first API is the intraocular pressure lowering agent and the second API is the NPR-B.

Embodiment 85. The drug delivery system of Embodiment 81, further comprising a second API, wherein the first API is the intraocular pressure lowering agent and the second API is the FAS inhibitor or the FASL inhibitor.

Embodiment 86. The drug delivery system of Embodiment 81, further comprising a second API, wherein the first API is the neurotrophic agent and the second API is the CNP.

Embodiment 87. The drug delivery system of Embodiment 81, further comprising a second API, wherein the first API is the neurotrophic agent and the second API is the NRP-B.

Embodiment 88. The drug delivery system of Embodiment 81, further comprising a second API, wherein the first API is the neurotrophic agent and the second API is the FAS inhibitor or the FASL inhibitor.

Embodiment 89. The drug delivery system of Embodiment 81, further comprising a second API, wherein the first API is the CNP and the second API is the NRP-B.

Embodiment 90. The drug delivery system of Embodiment 81, further comprising a second API, wherein the first API is the CNP and the second API is the FAS inhibitor or the FASL inhibitor.

Embodiment 91. The drug delivery system of Embodiment 81, further comprising a second API, wherein the first API is the NRP-B and the second API is the FAS inhibitor or the FASL inhibitor.

Embodiment 92. The drug delivery system of Embodiment 81, 82, 83, 84, 85, 86, 87, 88, 89, 90, or 91, wherein the first API and the second API are not covalently bonded to one another.

Embodiment 93. The drug delivery system of Embodiment 81, 82, 83, 84, 85, 86, 87, 88, 89, 90, or 91, wherein the first API is covalently bonded to the second API.

Embodiment 94. The drug delivery system of Embodiment 81, 82, 83, 84, 85, 86, 87, 88, 89, 90, 91, 91, 92, or 93, wherein the first API is covalently bonded to the sustained delivery component.

Embodiment 95. The drug delivery system of Embodiment 81, 82, 83, 84, 85, 86, 87, 88, 89, 90, 91, 92, 93, or 94, wherein the second API is covalently bonded to the sustained delivery component.

Embodiment 96. The drug delivery system of Embodiment 81, 82, 83, 84, 85, 86, 87, 88, 89, 90, 91, 92, 93, 94, or 95, having about 100 µg to about 1 mg of the first API.

Embodiment 97. The drug delivery system of Embodiment 81, 82, 83, 84, 85, 86, 87, 88, 89, 90, 91, 92, 93, 94, 95, or 96, having about 100 µg to about 1 mg of the second API.

Embodiment 98. The drug delivery system of Embodiment 81, 82, 83, 84, 85, 86, 87, 88, 89, 90, 91, 92, 93, 94, 95, 96, or 97, wherein the implant has a weight of about 300 µg to about 10 mg.

Embodiment 99. A method of treating a glaucoma comprising administering a drug delivery system of Embodiment 81, 82, 83, 84, 85, 86, 87, 88, 89, 90, 91, 92, 93, 94, 95, 96, 97, or 98 to a mammal in suffering from glaucoma or ocular hypertension.

Embodiment 100. The method of Embodiment 99, wherein the drug delivery system is injected into an eye of the mammal.

Embodiment 101. The method of Embodiment 99 or 100, wherein the mammal is a human being.

Embodiment 102. Use of an intraocular pressure lowering agent, a neurotrophic agent, a CNP, an NPR-B, a FAS inhibitor or a FASL inhibitor, or a combination thereof, in the manufacture of a drug delivery system for the treatment of glaucoma or ocular hypertension, wherein the drug delivery system further comprises a sustained delivery component.

Embodiment 103. The use of Embodiment 102, wherein the drug delivery system is injected into an eye of the mammal.

Embodiment 104. The use of Embodiment 102 or 103, wherein the mammal is a human being.

Embodiment 105. A kit comprising a drug delivery system of Embodiment 81, 82, 83, 84, 85, 86, 87, 88, 89, 90, 91, 92, 93, 94, 95, 96, 97, or 98 and a label with instructions for use of the drug delivery system for the treatment of a glaucoma.

Embodiment 106. The kit of Embodiment 105, wherein the drug delivery system is injected into the eye of the mammal.

The invention claimed is:

1. A method of treating a glaucoma or ocular hypertension comprising implanting a drug delivery system comprising a prostaglandin compound and a sustained delivery component, into a vitreous humour of an eye of a human being in need thereof, wherein the entire drug delivery system is biodegradable or bioerodible, wherein administering the drug delivery system to the vitreous humour of the eye of the human being results in a reduction in the intraocular pressure of the eye of the human being for at least one month with a risk of cystoid macular edema that is sufficiently low to be clinically acceptable, wherein the drug delivery system provides, to the vitreous humour of the eye of the human being, a dose of about 4 μg to about 40 μg of the prostaglandin compound over a period of four weeks.

2. The method of claim 1, wherein the drug delivery system further comprises Peptide 6, Peptide 21, or contains the amino acid sequence YLGA.

3. The method of claim 1, wherein the prostaglandin compound is bimatoprost amide, bimatoprost acid or a salt thereof.

4. The method of claim 1, wherein the drug delivery system further comprises MET4-8.

5. The method of claim 1, wherein the drug delivery system further comprises a peptide comprising the amino acid sequence DGGL (SEQ ID NO: 20) or a salt thereof.

6. The method of claim 1, wherein the reduction in the intraocular pressure in the eye of the human being occurs for a period of at least 3 months after the drug delivery system is implanted into vitreous of the eye of the human being.

7. The method of claim 1, wherein the drug delivery system is implanted into vitreous of the eye of the human being every 1 to 3 months.

8. The method of claim 1, wherein the drug delivery system is implanted into vitreous of the eye of the human being every 3 to 6 months.

9. The method of claim 1, wherein the drug delivery system is implanted into vitreous of the eye of the human being every 6 to 12 months.

10. The method of claim 1, wherein the drug delivery system is implanted into vitreous of the eye of the human being every 12 to 24 months.

11. The method of claim 1, wherein the drug delivery system has a mass of about 10 μg to about 100 mg.

12. The method of claim 1, wherein the drug delivery system has a mass of about 10 μg to about 100 μg.

13. The method of claim 1, wherein the drug delivery system has a mass of about 100 μg to about 1 mg.

14. The method of claim 1, wherein the drug delivery system has a mass of about 1 mg to about 100 mg.

15. The method of claim 1, wherein the drug delivery system contains about 1% to about 10% of the prostaglandin compound by weight.

16. The method of claim 1, wherein the drug delivery system contains about 10% to about 20% of the prostaglandin compound by weight.

17. The method of claim 1, wherein the drug delivery system contains about 20% to about 30% of the prostaglandin compound by weight.

18. The method of claim 1, wherein the drug delivery system contains about 30% to about 40% of the prostaglandin compound by weight.

19. The method of claim 1, wherein the drug delivery system contains about 40% to about 50% of the prostaglandin compound by weight.

* * * * *